(12) United States Patent
Khoshnan et al.

(10) Patent No.: US 7,803,758 B2
(45) Date of Patent: Sep. 28, 2010

(54) I KAPPA B KINASE COMPLEX AS A TARGET FOR THE TREATMENT OF HUNTINGTON'S DISEASE

(75) Inventors: Ali Khoshnan, South Pasadena, CA (US); Paul H. Patterson, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/869,501

(22) Filed: Oct. 9, 2007

(65) Prior Publication Data

US 2008/0112947 A1 May 15, 2008

Related U.S. Application Data

(63) Continuation of application No. 11/218,924, filed on Sep. 1, 2005, now Pat. No. 7,279,288.

(60) Provisional application No. 60/606,969, filed on Sep. 3, 2004.

(51) Int. Cl.
*A61K 38/00* (2006.01)
*A61K 49/00* (2006.01)
*G01N 33/53* (2006.01)
*G01N 33/567* (2006.01)
*C12Q 1/66* (2006.01)

(52) U.S. Cl. ............................ 514/2; 424/9.1; 435/7.21

(58) Field of Classification Search ........................ None
See application file for complete search history.

(56) References Cited

U.S. PATENT DOCUMENTS

| 6,649,654 | B1 | 11/2003 | Karin et al. |
| 6,869,956 | B2 | 3/2005 | Burke et al. |
| 7,122,544 | B2 | 10/2006 | Kois et al. |
| 2003/0232888 | A1 | 12/2003 | Karin et al. |
| 2006/0079543 | A1 | 4/2006 | Sum et al. |
| 2007/0244140 | A1 | 10/2007 | Hu et al. |

OTHER PUBLICATIONS

Karin et al. Nat Rev. Drug Dis. Jan. 2004. 3: 17-26.*
Li et al. Trends in Genetics 2004. 20:146-154.*
Burgess et al. J of Cell Bio. 1990, 111:2129-2138.*
Chien et al., Proc. Natl. Acad. Sci. USA, 88:9578-9582 (1991).
Dai et al., J. Biol. Chem. 279(36):37219 (2004).
Davies et al., Cell 90:537-548 (1997).
Edgerton et al., J Physiol (Lond) 548:53-69 (2003).
Jimi, et al., Na. Med. 10(6):617 (2004).
Ferrigno et al., "Polyglutamine Expansions. Proteolysis, Chaperones, and the Dangers of Promiscuity," *Neuron* vol. 26, Issue 1, pp. 9-12 (Apr. 2000).
Ghosh et al., Annu Rev Immunol 16:225-260 (1998).
Ghosh et al., Cell suppl. 109:81-96 (2002).
Gines et al., J Biol Chem 278:50514-50522 (2003).
The Huntington's Disease Collaborative Research Group, "A Novel Gene Containing a Trinucleotide Repeat That is Expanded and Unstable on Huntington's Disease Chromosomes," *Cell*, vol. 72, 971-983 (Mar. 26, 1993).
Houghten et al., Nature 354:84-86 (1991).
Karin and Lin, Nat Immunol 3:221-227 (2002).
Khoshnan et al., "Effects of intracellular expression of anti-huntingtin antibodies of various specificities on mutant huntingtin aggregation and toxicity," *PNAS*, vol. 99, No. 2, pp. 1002-1007 (Jan. 22, 2002).
Ko et al., "New anti-huntingtin monoclonal antibodies: Implications for Huntingtin conformation and its binding proteins," *Brain Research Bulletin*, vol. 56, Nos. 3/4, pp. 319-329 (2001).
Lam et al., Nature 354:82-84 (1991).
Li et al., "A huntingtin-associated protein enriched in brain with implications for pathology," *Nature*, 278, 398-402 (Nov. 23, 1995).
Lin et al., "Sequence of the murine Huntington disease gene: evidence for conservation, and polymorphism in a triplet (CCG) repeated alternate splicing," *Human Molecular Genetics*, vol. 3, No. 1, pp. 85-92 (1994).
May et al., Science 289:1550(2000).
Menalled et al., "Decrease in Striatal Enkephalin mRNA in Mouse Models of Huntington's Disease," *Experimental Neurology*, vol. 162, Issue 2, pp. 328-342 (Apr. 2000).
Mende-Mueller, "Tissue Specific Proteolysis of Huntingtin (htt) in Human Brain: Evidence of Enhanced Levels of N- and C-Terminal htt Fragments in Huntington's Disease Striatum," *The Journal of Neuroscience*, 21(6), pp. 1830-1837 (Mar. 15, 2001).
Ogino et al., Mol Pharmacol. 65(6):1344-51 (2204).
Onodera et al., "Toxicity of expanded polyglutamine-domain proteins in *Escherichia coli*," *Febs Letters*, vol. 399, Issues 1-2, pp. 135-139 (Dec. 9, 1996).

(Continued)

*Primary Examiner*—Christine J Saoud
*Assistant Examiner*—Chang-Yu Wang
(74) *Attorney, Agent, or Firm*—Knobbe, Martens, Olson & Bear, LLP

(57) ABSTRACT

The present invention provides methods and compositions for protecting cells from the toxicity of mutant huntingtin (Htt) protein and for treatment of Huntington's disease (HD). The methods generally involve administering to cells or a patient an effective amount of an IKK inhibitor. In addition, methods are provided for identifying therapeutics for the treatment of HD.

12 Claims, 14 Drawing Sheets

OTHER PUBLICATIONS

Pahl, *Oncogene* 18:6853-6866 (1999).

Platt *J. Biol. Chem.* 269:28588-28562 (1994).

Poyet et al., *J Biol Chem* 275:37966-37977 (2000).

Reddy et al., "Recent advances in understanding the pathogenesis of huntington's disease", Elsevier Science, 1999, p. 248-255, vol. 22, No. 6.

Ross, Christopher A., "Intranuclear Neuronal Inclusions: A Common Pathogenic Mechanism for Glutamine-Repeat Neurodegenerative Diseases?" *Neuron*, vol. 19, Issue 6, pp. 1147-1150 (Dec. 1997).

Rubinsztein et al., "Site of (CCG) polymorphism in the HD gene," *Nature Genetics*, 5, pp. 214-215 (1993).

Sugars et al., *J Biol Chem* 279:4988-4999 (2004).

Tobin et al., "Huntington's disease: the challenge for cell biologists," *Trends in Cell Biology*, vol. 10, Issue 12, pp. 531-536 (Dec. 1, 2000).

Trottier et al., "Cellular localization of the Huntington's disease protein and discrimination of the normal and mutated form," *Nature Genetics*, 10, pp. 104-110 (1995).

Trottier et al., "Polyglutamine expansion as a pathological epitope in Huntington's disease and four dominant cerebellar ataxias," *Nature*, 378, pp. 403-406 (Nov. 23, 1995).

Wanker, Erich E., "Protein Aggregation and Pathogenesis of Huntington's Diseases: Mechanisms and Correlations," *Biol. Chem.*, vol. 381, pp. 937-942 (Sep./Oct. 2000).

Wheeler et al., "Long glutamine tracts cause nuclear localization of a novel form of huntingtin in medium spiny striatal neurons in $Hdh^{Q92}$ and $Hdh^{Q111}$ knock-in mice," *Human Molecular Genetics*, vol. 9, No. 4, pp. 503-513 (2000).

Zoghbi et al., "Glutamine Repeats and Neurodegeneration", *Annu. Rev. Neurosci.*, 2000, p. 214-247.

Burke et al., "BMS-345541 is a highly selective inhibitor of IκB kinase that binds at an allosteric site of the enzyme and blocks NF-κB-dependent transcription in mice," *J. Biol. Chem.*, 278(3):1450-1456, 2003.

Cho et al., "Brain slices as models for neurodegenerative disease and screening platforms to identify novel therapeutics," *Current Neuropharmacology*, 2007, 5:19-33, 2004.

Kapahi et al., "Inhibition of NF-κB Activation by arsenite through reaction with a critical cysteine in the activation loop of IκB kinase," *J. Biol. Chem.* 275(46):36062-36066, 2000.

Khoshnan et al. "IKKα and IKKβ regulation of DNA damage-induced cleavage of Huntingtin," *PlosOne*, 6:e5768, 2009.

Ojo-Amaize et al., "Hypoestoxide, a novel anti-inflammatory natural diterpene, inhibits the activity of IκB kinase," *Cell. Immunol.*, 209:149-157, 2001.

Rossi et al., "Anti-inflammatory cyclopentenone prostaglandins are direct inhibitors of IκB kinase," *Nature*, 403:103-108, 2000.

Yin et al., "The anti-inflammatory agents aspirin and salicylate inhibit the activity of IκB kinase-β," *Nature*, 396:77-80, 1998.

* cited by examiner

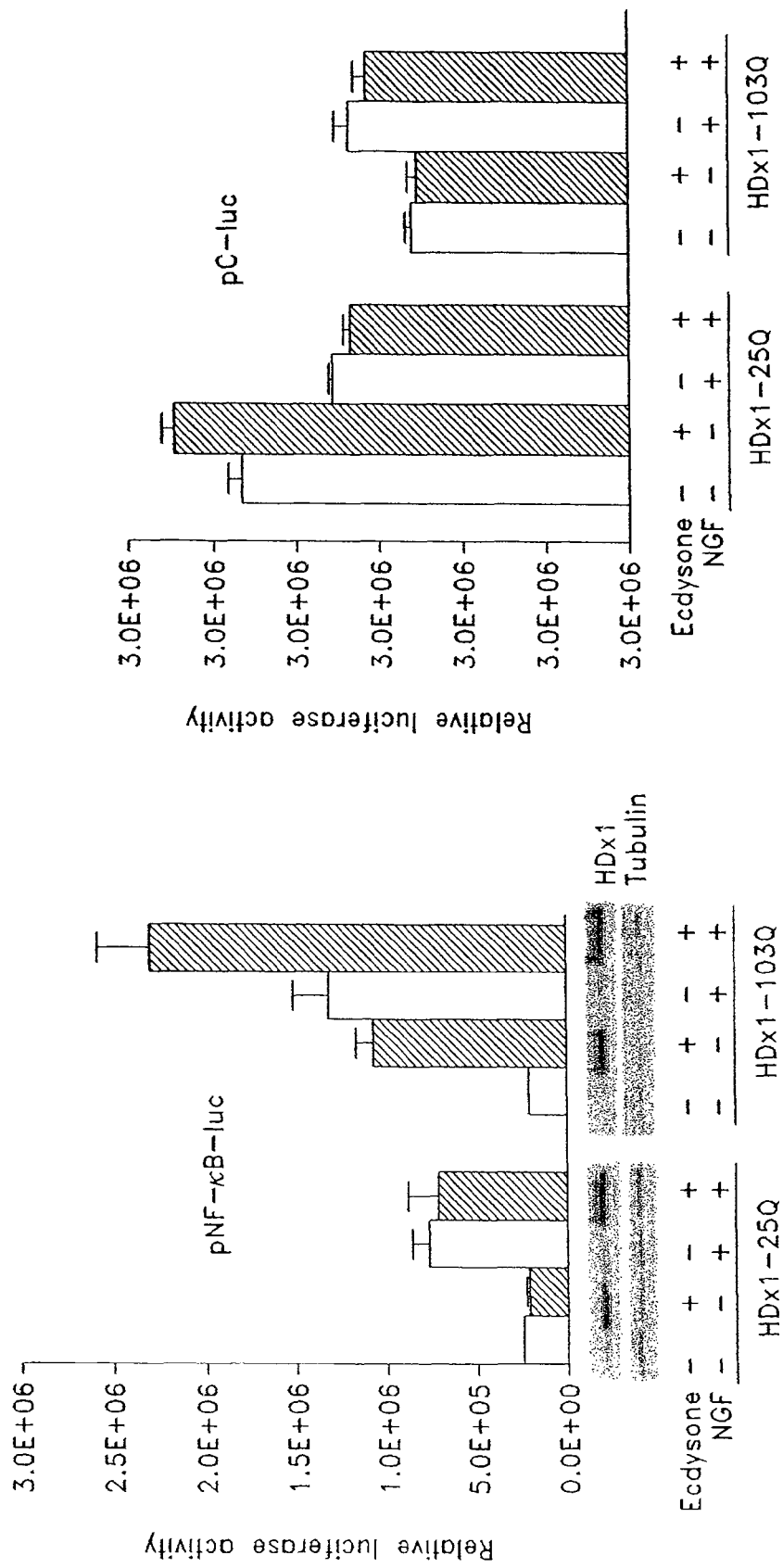

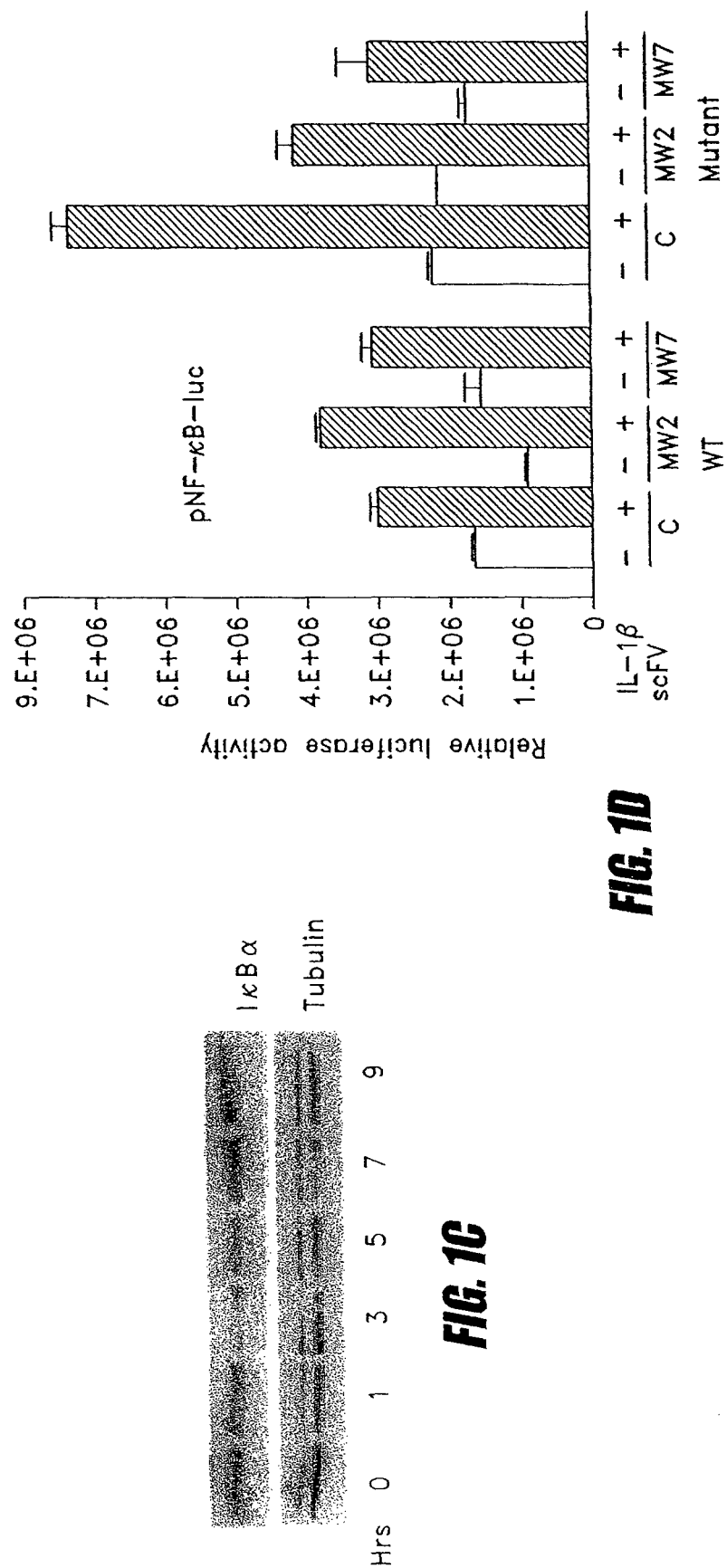

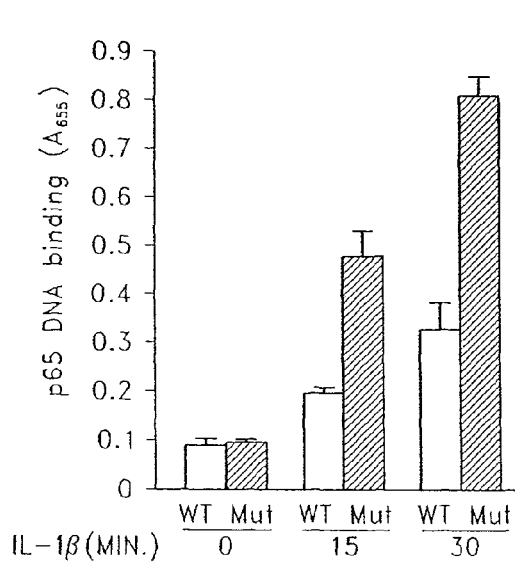
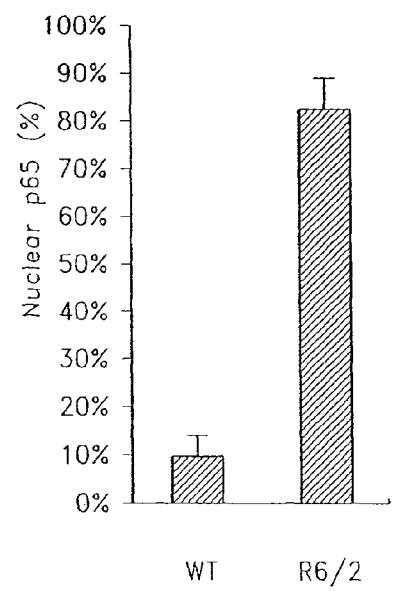
FIG. 2A    FIG. 2B

FIG. 3A
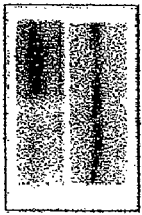
FIG. 3B
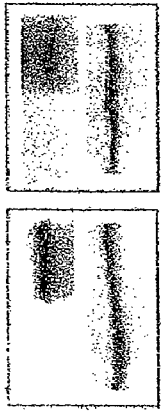
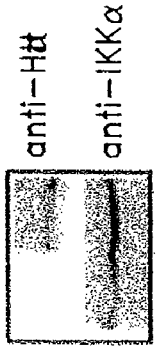
FIG. 3C
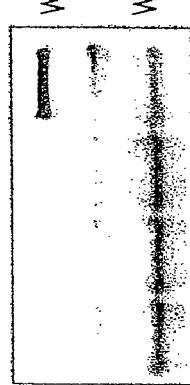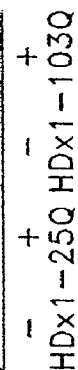
FIG. 3E
FIG. 3D

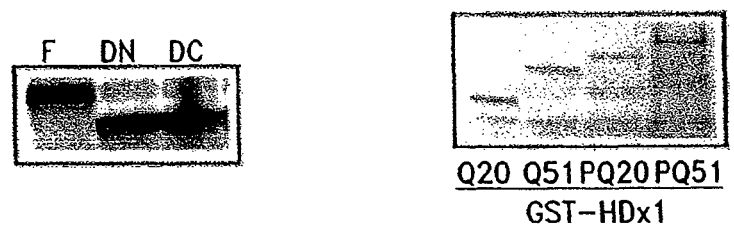
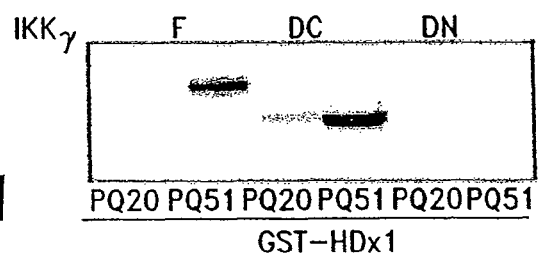
FIG. 4A
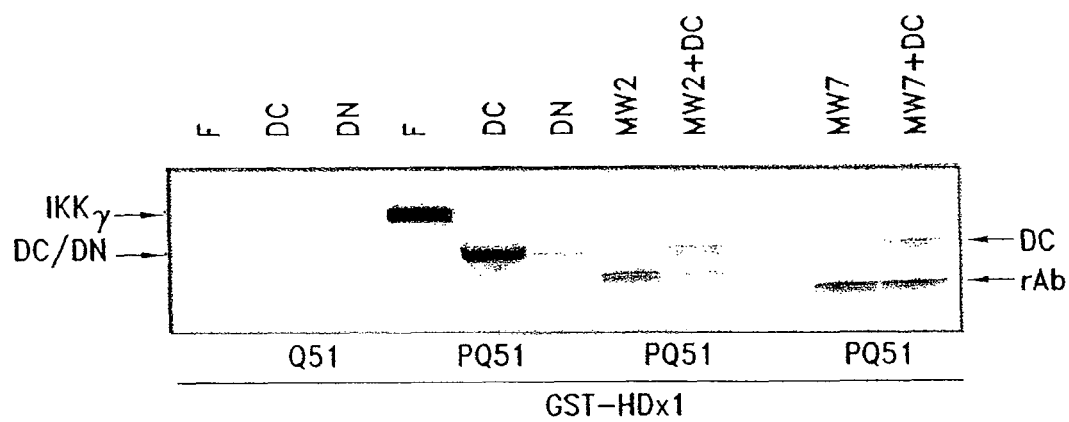
FIG. 4B

I KAPPA B KINASE COMPLEX AS A TARGET FOR THE TREATMENT OF HUNTINGTON'S DISEASE

CROSS-REFERENCE TO RELATED APPLICATIONS

This application is a continuation of U.S. patent application Ser. No. 11/218,924, filed Sep. 1, 2005, which claims priority under 35 U.S.C. §119(e) to U.S. Provisional Application No. 60/606,969, filed Sep. 3, 2004. The priority application is incorporated herein by reference in its entirety.

STATEMENT REGARDING FEDERALLY SPONSORED R&D

This invention was made with government support under grant NS045165-01A1 awarded by the National Institutes of Neurological Disorders and Stroke. The government has certain rights in the invention.

BACKGROUND OF THE INVENTION

1. Field of the Invention

The present invention relates generally to targets for treating Huntington's disease, and more specifically to methods and compositions for protecting cells from the toxicity of mutant Htt and treating Huntington's disease in an animal.

2. Description of the Related Art

Huntington's disease (HD) is a fatal autosomal dominant neurodegenerative disorder that is caused by the expansion of CAG repeats in exon 1 (HDx1) of huntingtin gene (Reddy et al. *Trends Neurosci.* 22:248-255 (1999)). The huntingtin gene is known and is the subject of U.S. Pat. No. 5,693,757, incorporated herein by reference. Expanded CAG repeats (40 and above), which form an abnormal polyglutamine (polyQ) stretch in the huntingtin (Htt) protein, result in a gain of toxic function and induce death in subpopulations of neurons in the striatum and cortex (Zoghbi et al. *Annu. Rev. Neurosci.* 23:217-247 (2000); Tobin et al. *Trends Cell Biol.* 10:531-536 (2000)). Neuronal death in HD has been attributed not only to polyQ toxicity, but also to activation of caspases, transcriptional dysregulation, and sequestration/inactivation of wild-type Htt and other important cellular factors. As disclosed below, the NF-κB pathway, which plays a central role in cell death and survival, is effected by mutant Htt.

NF-κB is sequestered in the cytoplasm by a family of inhibitory proteins (Iκ-Bs) (Ghosh et al., *Annu Rev Immunol* 16:225-260 (1998)). Iκ-Bs are phosphorylated by a signal-activated kinase complex known as I-κB kinase (IKK) (Ghosh and Karin, *Cell* [Suppl] 109:81-96 (2002)). This complex contains two catalytic subunits, IKKα and IKKβ, and a regulatory module, IKKγ (Karin and Lin, *Nat Immunol* 3:221-227 (2002)). Phosphorylated Iκ-Bs are ubiquitinated by an F-box E3-ligase, β-transducin repeat-containing protein (β-TrCP) (Spencer et al., *Genes Dev* 13:284-294 (1999)) and subsequently degraded by proteosomes. Liberated NF-κB can bind DNA and promote gene expression (Pahl, *Oncogene* 18:6853-6866 (1999)).

SUMMARY OF THE INVENTION

In one aspect, the invention relates to methods for protecting cells, preferably in a mammal, from the toxicity of mutant Htt by blocking activation of IKK. This may be done by administering to the mammal an effective amount of an IKK inhibitor. In another aspect, the invention relates to methods for treatment of HD by administering an effective amount of an IKK inhibitor to a patient. In some embodiments the IKK inhibitor blocks activation of IKK.

Preferably, the IKK inhibitor acts directly on IKK. However, in some embodiments the IKK inhibitor may inhibit the activity of a molecule in a downstream IKK dependent pathway, such as βTrCP. In other embodiments the inhibitor may block the interaction between IKK and mutant Htt. Preferred molecules useful for inhibiting IKK include small molecule inhibitors, antibodies, dominant negative forms of IKK, such as DN-IKKγ, and dominant negative forms of the E3-ubiquitin ligase βTrCP, such as ΔF-βTrCP. In some embodiments the IKK inhibitor binds to one or more subunits of IKK, such as IKKβ. The IKK inhibitor may block the interaction of IKK subunits, such as the interaction of IKKγ with IKKβ or IKKα. In another embodiment, the IKK inhibitor blocks IKKβ activation.

In some embodiments, the IKK inhibitor is a small molecule selected from the group consisting of herbimycin, NEMO binding peptide, sodium salicylate, retinoid-related compounds, and cyclopentenone prostaglandins. In another embodiment, the IKK inhibitor is an antibody. In still other embodiments, the IKK inhibitor is an antibody, such as a monoclonal antibody that inhibits IKK activity.

In another aspect, the methods of the invention involve the treatment of an individual, more preferably a mammal and even more preferably a human having, suspected of having and/or at risk of developing HD by administering a therapeutically effective amount of an IKK inhibitor to the individual. In preferred embodiments the IKK inhibitor compositions of the methods are preferably delivered intracranially, for example, by injection directly into brain tissue or by injection into the cerebrospinal fluid. However, in other embodiments, for example where the IKK inhibitor is able to cross the blood brain barrier, the IKK inhibitor is administered peripherally.

In another aspect, the present invention provides an article of manufacture that comprises a container, a pharmaceutical composition comprising an IKK inhibitor within the container and instructions to administer the pharmaceutical composition at a dose which is between about 0.01 µg/kg and about 1 mg/kg.

In another aspect, the present invention provides methods of screening for an IKK inhibitor useful for protecting cells, preferably in a mammal, from the toxicity of mutant Htt. Preferably the IKK inhibitor blocks activation of IKK. IKK inhibitors that are identified can be used for treating HD.

BRIEF DESCRIPTION OF THE DRAWINGS

FIG. 1 shows mutant Htt activates NF-κB-dependent gene expression. A, is a graph illustrating that PC12 cells expressing mutant HDx1 show elevated NF-κB activity. The graph shows luciferase units from a plasmid with a minimal promoter containing NF-κB binding sites. B, is a graph illustrating that expression of WT or mutant HDx1 does not influence luciferase expression from a control plasmid, which lacks an NF-κB enhancer element. C, Is a western blot showing that NF-κB activation by mutant Htt includes degradation of Iκ-Bα. PC12 cells were treated with ecdysone to induce HDx1 for the indicated time and examined by Western blotting with anti-Iκ-Bα antibody. D, is a graph illustrating that full-length mutant Htt enhances IL-1β-mediated NF-κB activation. Striatal cells from WT and HD KI mice were transfected with NF-κB or the control reporter and the indicated plasmids.

FIG. 3 shows that mutant HDx1 activates the IKK complex. A, is a blot IKK complexes isolated from PC12 cells expressing mutant HDx1 have elevated kinase activity. Similar results were obtained when IKK complexes were isolated from striatal or cortical extracts of HD transgenic R6/2 mice (B) or striatal HD knock-in mice (C). D, is a Western blot showing that mutant HDx1 coprecipitates with endogenous IKK complex. E, is a Western blot showing that mutant Htt coimmunoprecipitates with IKK complexes isolated from R6/2 striatal extracts.

DETAILED DESCRIPTION

Figure 2C:
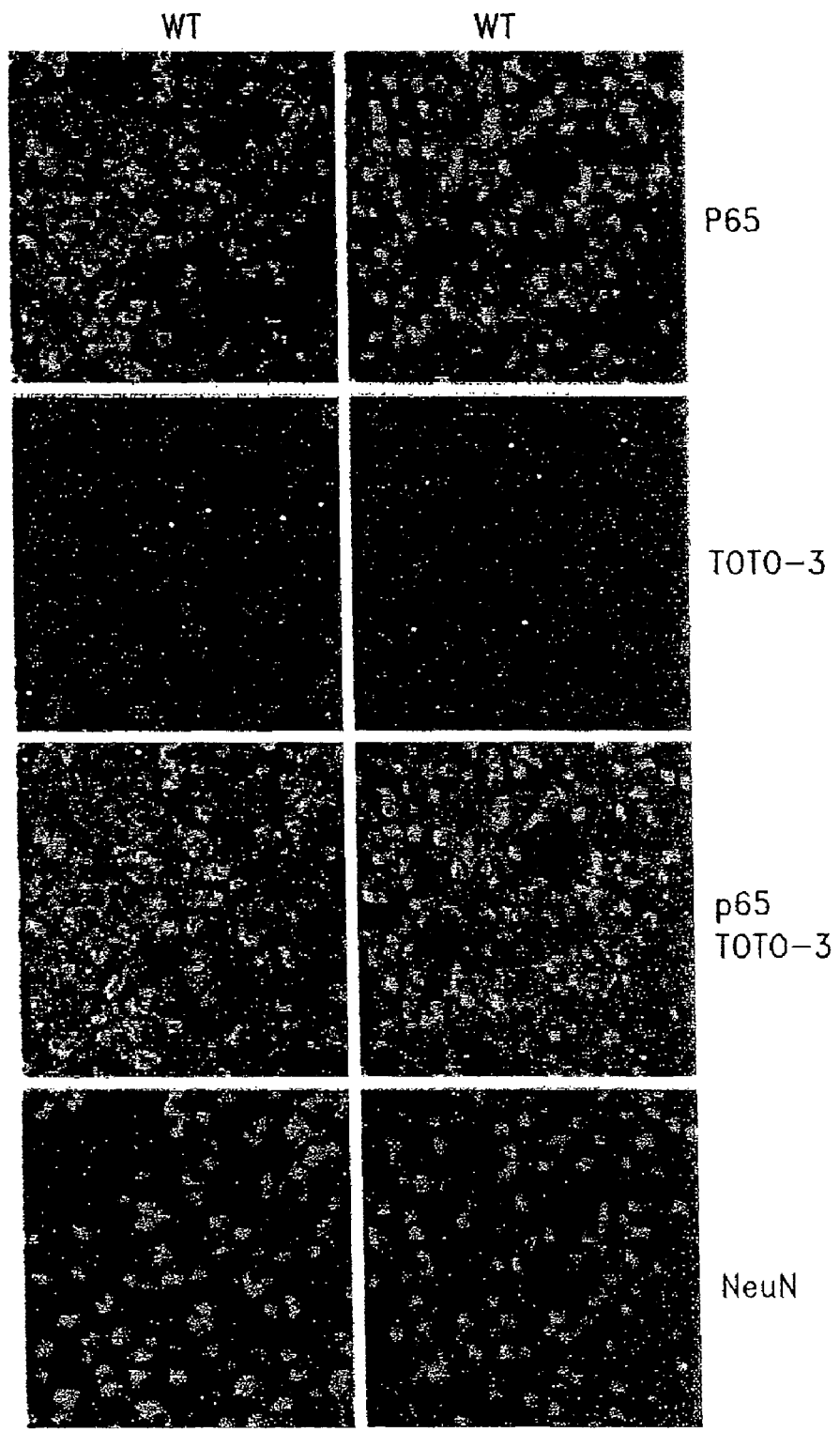
FIG. 2 shows that mutant Htt promotes activation of nuclear localization of NF-κB. A, is a graph illustrating binding of nuclear proteins from control and IL-1β-treated striatal cells from WT or mutant Htt KI mice to the oligonucleotide recognized by NF-κB. B, is a graph showing that the nuclear localization of the NF-κB p65 subunit is elevated in HD transgenic brain. C, is a micrograph of nuclear p65 staining showing the average percentage of positive neurons per microscopic field from 16 brain sections of four animals each for WT and HD mice.

One embodiment of the present invention is a treatment for Huntington's disease (HD). This embodiment is based, in part, on the discovery that inhibition of I-κB kinase (IKK) activity can protect against the toxicity associated with mutant huntingtin protein (Khoshnan et al., *Journal of Neuroscience* 24 (37) (2004)), expressly incorporated herein by reference) which leads to manifestation of HD in humans. In some embodiments cells are protected from the toxicity of mutant Htt by contacting the cells with an IKK inhibitor.

In other embodiments, patients suffering from Huntington's disease (HD) are treated by blocking IKK activation in vivo, as described in more detail below. Preferred molecules useful for inhibiting IKK include small organic molecules, peptides and antibodies. Compounds that inhibit IKK activity and are thus suitable for use in the methods of the present invention include, without limitation, herbimycin, NEMO binding peptides, sodium salicylate, retinoid-related compounds, and cyclopentenone prostaglandins. Herbimycin binds IKKβ and blocks activation of IKK. NEMO binding peptides block the interaction of IKKγ with IKKβ and IKKα, thereby blocking IKK activation. Sodium salicylate, retinoid-related compounds and cyclopentenone prostaglandins also inhibitors of IKKβ activation.

In other embodiments, compounds that can be used to treat HD are identified by screening compounds for their ability to inhibit IKK activity. Compounds that can be screened include, without limitation, small organic molecules, peptides and antibodies.

These and other embodiments are described in more detail below.

Definitions

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

"Huntingtin" and "Htt" refer broadly to the huntingtin gene and the protein encoded by the huntingtin gene, including mutant and variant forms as well as native forms. "Variants" are biologically active polypeptides having an amino acid sequence which differs from the sequence of a native sequence polypeptide. Native sequence human huntingtin protein is described, for example, by The Huntington's Disease Collaborative Research Group in *Cell* 72:971-983 (1993) as well as in Li et al. *Nature* 378:398-402 (1995) and WO 02/29408. The number of polyglutamine repeats in native huntingtin protein is known to vary, from about 13 to about 36 glutamine residues in the polyQ region of native human protein. Native sequence murine Htt is described, for example, in Lin et al. *Hum. Mol. Genet.* 3 (1), 85-92 (1994) and typically comprises about 7 glutamine residues in the polyQ region. Particular variants of the huntingtin gene will comprise different numbers of CAG repeats, resulting in variation in the polyglutamine region of the huntingtin protein.

"Mutant huntingtin protein" refers to huntingtin protein which differs in some respect from the native sequence huntingtin protein. Typically, mutant huntingtin will comprise an expanded polyglutamine or polyproline region compared to the native form. A preferred mutant huntingtin protein has an expanded polyglutamine region of 40 or more glutamine residues.

"IKK" refers broadly to the Iκ-B kinase complex. The Iκ-B kinase complex comprises two catalytic subunits IKKα and IKKβ and a regulatory subunit IKKγ.

The term "IKK inhibitor" is used in the broadest sense and includes any molecule that partially or fully blocks, inhibits or neutralizes a biological activity mediated by IKK, preferably by preventing the activation of IKK. Preferred IKK inhibitors act directly on one or more subunits of IKK, for example by binding to one or more subunits of IKK. However, in other embodiments the IKK inhibitors may prevent IKK from interacting with a substrate, such as I-κB and/or may act on molecules in an IKK signaling pathway, preferably downstream from IKK. In still other embodiments the IKK inhibitors may modulate the level of IKK gene expression or otherwise reduce the levels of IKK in affected cells.

The ability of a molecule to inhibit IKK activation can be measured using assays that are well known in the art. For example and without limitation, IKK inhibitors can be identified using immune complex kinase assays and gene reporter assays. Briefly, in an immune complex kinase assay, immunoprecipitated IKK complexes are examined for the ability to phosphorylate GST-IκBα in vitro. For example, IKK complexes can be immunoprecipitated from cleared striatal extracts from animals or cells treated with the putative IKK inhibitor by incubation with a mouse anti-IKKα antibody (Santa Cruz Biotechnology) coupled to protein-A beads and rocked for 3 hr at 4° C. Beads are washed, and IKK activity can be evaluated in vitro with 1 μg of purified GST-IκBα (N-terminal 61 amino acids) in the presence of 10 μCi of [$^{32}$P]γ-ATP for 30 min at 30° C. Products are examined by SDS-PAGE followed by autoradiography.

Gene reporter assays can be used to measure downstream effects of IKK, such as NF-κB activation. For example, a plasmid based reporter, pNF-κB-luciferase, with five enhancer elements and a control plasmid without NF-κB binding sites, pCIS-CK-luciferase, can be used to verify inhibition of NF-κB activity in cells treated with the putative inhibitor (Stratagene, La Jolla, Calif.). The skilled artisan will be able to select the appropriate assays and reaction conditions based on the particular circumstances.

Furthermore, the term "IKK inhibitor" includes any molecule that mimics a biological activity mediated by an IKK subunit and specifically changes the function or expression of IKK, or the efficiency of signaling through IKK, thereby inhibiting an already existing biological activity or triggering a new biological activity.

"Biological property" or "biological activity" is a biological function caused by an IKK, an IKK inhibitor, or other compound of the invention. Biological properties of IKKs include the phosphorylation of I-κB and activation of NF-κB dependent pathways. With regard to the IKK inhibitors, biological activity refers, in part, to the ability to inhibit activation of IKK. Other preferred biological activities of IKK inhibitors include prevention of cell death or apoptosis, inhibition of NF-κB dependent gene transcription and the ability to regulate and preferably reduce or eliminate the toxic effects of mutant huntingtin protein that are associated with neurodegenerative disease.

The term "therapeutically effective amount" or "therapeutically effective dose" refers to an amount effective to treat a disease or disorder in a mammal. In the case of HD, the therapeutically effective amount of an IKK inhibitor prevents cell death associated with mutant Htt and/or reduces one or more of the symptoms of HD. The therapeutically effective dose may be a single dose, or may comprise multiple doses given over a period of time.

The term "antibody" is used herein in the broadest sense and specifically covers human, non-human (e.g. murine) and humanized monoclonal antibodies, including full length monoclonal antibodies, polyclonal antibodies, multi-specific antibodies, and antibody fragments, including intrabodies, so long as they exhibit a desired biological activity. Antibodies exhibit binding specificity to a specific antigen.

An "individual" is a vertebrate, preferably a mammal, more preferably a human.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

As used herein, "treatment" is a clinical intervention made in response to and in anticipation of a disease, disorder or physiological condition manifested by a patient, particularly Huntington's disease. The aim of treatment includes the alleviation or prevention of symptoms, slowing or stopping the progression or worsening of a disease, disorder or condition and/or the remission of the disease, disorder or condition.

"Treatment" refers to both therapeutic treatment and prophylactic or preventative measures. Those in need of treatment include those already affected by a disease or disorder or undesired physiological condition as well as those in which the disease or disorder or undesired physiological condition is to be prevented.

In the methods of the present invention, the term "control" and grammatical variants thereof, are used to refer to the prevention, partial or complete inhibition, reduction, delay or slowing down of an unwanted event, such as the presence or onset of Huntington's disease.

IKK Inhibitors

In some embodiments of the invention, cells are protected from the toxicity of mutant Htt protein by administering an effective amount of an IKK inhibitor. In other embodiments HD is treated by administering an IKK inhibitor to a patient. A variety of molecules are known to inhibit IKK activity and can be used to reduce toxicity of Htt in cells or to treat a patient having or expected to develop HD. The method by which IKK is inhibited is not limited in any way, and may be, for example, by blocking IKK subunit interaction. In addition, the present invention provides methods for screening for molecules useful for reducing toxicity of Htt in cells and for treating HD.

In some embodiments, the IKK inhibitor preferably interacts with IKK and blocks activation. However, in other embodiments the IKK inhibitor may interfere with the interaction of IKK with a binding partner or substrate or may interfere with IKK gene expression or otherwise modulate the levels of IKK in the body. In still other embodiments the IKK inhibitor may interact with a molecule that is in an IKK dependent pathway, preferably downstream from IKK.

The type of IKK inhibitor is not limited in any way. Preferred IKK inhibitors include, for example, small molecule inhibitors, antibodies, proteins, etc. In one embodiment, the IKK inhibitor is a small molecule that binds to IKKβ, for example a Src tyrosine kinase inhibitor such as herbimycin. Herbimycin A abrogates NF-κB activation by interacting with the IKKβ subunit (Ogino et al., *Mol. Pharmacol.* 65(6): 1344-51 (2004)). In other embodiments the IKK inhibitor is a compound that blocks interaction of IKK subunits, such as the interaction of IKKγ with IKKβ and IKKα. An example of such a compound is a NEMO (IKKγ) binding peptide (see, for example, Dai et al. *J. Biol. Chem.* 279(36):37219 (2004); Eijiro, J., et al. *Nat. Med.* 10(6):617 (2004); Siegmund, D., et al. *J. Biol. Chem.* 276:43708 (2001); May, M. J., et al. *Science* 289:1550 (2000); and Li, Q., et al. *Science* 284:1999 (1999), incorporated by reference herein). A NEMO binding peptide that is used in some embodiments is available from Calbiochem (Cat. No. 480025). In another embodiment, the IKK inhibitor is a compound that blocks IKKβ activation, for example, sodium salicylate. In another embodiment, the IKK inhibitor is a retinoid-related compound or a cyclopentenone prostaglandin.

In other embodiments the inhibitor is a compound that blocks the interaction of IKK with mutant Htt. In some such embodiments the compound that blocks the interaction of IKK with mutant Htt is a peptide or small organic molecule. Preferably the compound binds IKK.

Antibodies that can block activation of IKK are also suitable for use in methods of the present invention. Preferred antibodies bind to one or more subunits of the IKK complex. For example, antibodies that are targeted to one or more subunits of IKK and prevent interaction of the subunits can be used. In other embodiments an antibody that prevents IKK from phosphorylating I-κB can be used. In still other embodiments an anti-IKK antibody prevents interaction of IKK and mutant Htt. The antibodies are not limited in any way, but are preferably monoclonal antibodies, more preferably human or humanized monoclonal antibodies. Antibodies to IKK can be prepared using methods that are well known in the art and inhibitory antibodies can be identified using the methods described herein.

Figure 7C:
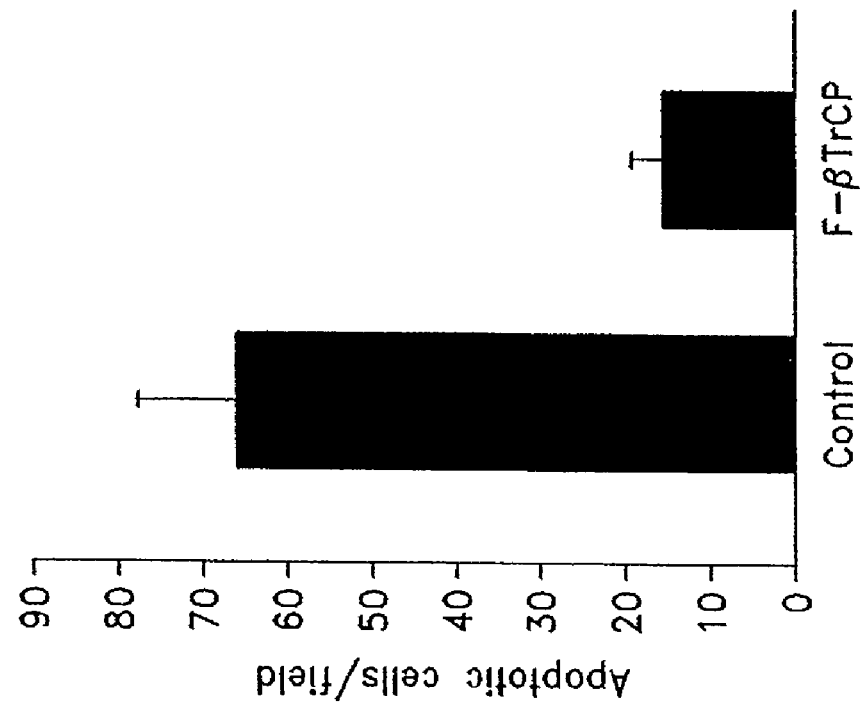
FIG. 7 shows ΔF-βTrCP reduces the toxicity of mutant Htt. A, is a graph illustrating that NF-κB activation by mutant HDx1 is blocked by ΔF-βTrCP. B, is a series of micrographs showing that mutant HDx1 and ΔF-βTrCP are colocalized in living HEK-293 cells. C, is a graph illustrating that apoptotic bodies in transfected HEK-293 cells are reduced by ΔF-βTrCP. D, is a graph illustrating that expression of ΔF-βTrCP reduces the toxicity of mutant HDx1 in MSNs.
Figure 7A:
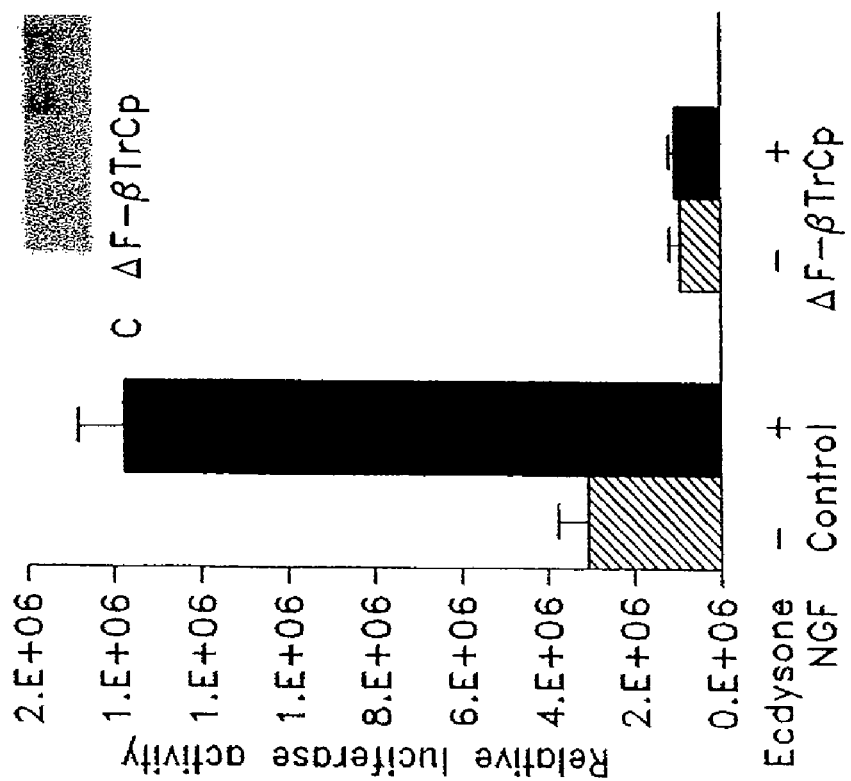

Other proteins that can block activation of IKK or otherwise inhibit IKK activity are also suitable for use in the methods of the present invention. For example, expression of DN-IKKγ or ΔF-βTrCP reduces the toxicity of mutant Htt in cell culture and protects striatal MSNs in a brain slice model of HD. DN-IKKγ lacks the binding domain essential for interaction with IKKα and -β and thus inhibits IKK activity (May et al., Science 289:1550-1554 (2000); Poyet et al., *J Biol Chem* 275:37966-37977 (2000)). DN-IKKγ also blocks basal and NGF-induced NF-κB-dependent gene expression by mutant HDx1 in inducible PC12 cells (FIG. 5C). The E3-ubiquitin ligase βTrCP specifically promotes degradation of Iκ-Bα (Spencer et al., *Genes Dev* 13:284-294 (1999)). A dominant-negative form of βTrCP, ΔF-βTrCP, blocks degradation of phosphorylated Iκ-Bs and abolishes basal and mutant HDx1-induced NF-κB activity (FIG. 7A). Thus, DN-IKKγ, and ΔF-βTrCP can be used to block IKK activation for purposes of the present invention.

In some embodiments proteins that are able to block IKK activation are provided directly to the patient, such as by injection. In other embodiments nucleic acids encoding the proteins are obtained and inserted into appropriate expression vectors. Cells that may be subject to mutant Htt toxicity may then be transfected with the expression vector, such that the protein is expressed in the cells. Methods for such genetic therapies are known in the art and can be adapted by the skilled artisan as necessary. This includes both gene therapy where a lasting effect is achieved by a single treatment, and gene therapy where the increased expression is transient. Selective expression of IKK inhibitory proteins in appropriate cells may be achieved by using vectors with tissue specific or inducible promoters or by producing localized infection with replication defective viruses, or by any other method known in the art.

Compositions Comprising IKK Inhibitors

One embodiment of the invention is a method of treatment involving administration of an effective amount of a composition comprising an IKK inhibitor. In some embodiments, the composition comprises an IKK inhibitor that is a small molecule or peptide, for example an IKK inhibitor selected from the group consisting of herbimycin, NEMO binding peptide, sodium salicylate, retinoid-related compounds, and cyclopentenone prostaglandins. In other embodiments the composition comprises an IKK inhibitor that is an antibody or other polypeptide, such as a human or humanized anti-IKK monoclonal antibody.

In pharmaceutical dosage forms, the IKK inhibitors may be used alone or in appropriate association, as well as in combination with other pharmaceutically active or inactive compounds. The IKK inhibitors can be formulated into pharmaceutical compositions containing a single IKK inhibitor or a combination of two or more IKK inhibitors. For example, a pharmaceutical composition can contain two or more different IKK inhibitors. In one embodiment, the pharmaceutical composition contains two or more different IKK inhibitors having the same mode of action. For example, both IKK inhibitors may disrupt subunit interaction. In another embodiment, the pharmaceutical composition contains two or more IKK inhibitors having different methods of action. For example, one inhibitor may disrupt subunit interaction while a different inhibitor prevents IKK from phosphorylating I-κB.

The IKK inhibitors can be formulated into pharmaceutical compositions by combination with appropriate, pharmaceutically acceptable carriers or diluents (Remington, *The Science and Practice of Pharmacy*, 19$^{th}$ Edition, Alfonso, R., ed., Mack Publishing Co., Easton, Pa. (1995)), and may be formulated into preparations in solid, semi-solid, liquid or gaseous forms, such as tablets, capsules, powders, granules, ointments, solutions, suppositories, injections, inhalants and aerosols depending on the particular circumstances.

The pharmaceutically acceptable excipients, such as vehicles, adjuvants, carriers or diluents, are readily available. Moreover, pharmaceutically acceptable auxiliary substances, such as pH adjusting and buffering agents, antioxidants, low molecular weight (less than about 10 residues) polypeptides, tonicity adjusting agents, stabilizers, wetting agents and the like, are readily available. "Carriers" when used herein refers to pharmaceutically acceptable carriers, excipients or stabilizers which are nontoxic to the cell or mammal being exposed to the carrier at the dosages and concentrations used.

The IKK inhibitors to be used for in vivo administration are preferably sterile. The sterility may be accomplished by any method known in the art, such as by filtration using sterile filtration membranes, prior to or following lyophilization and reconstitution. In some embodiments the IKK inhibitors are available commercially in sterile form.

The IKK inhibitor compositions may be placed into a container with a sterile access port, for example, an intravenous solution bag or vial having a stopper pierceable by a hypodermic injection needle.

The inhibitors can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing or dispersing agents. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

For oral preparations, the IKK inhibitors can be combined with appropriate additives to make tablets, powders, granules or capsules. For example, the IKK inhibitor can be combined with conventional additives such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Liquid preparations for oral administration can take the form of, for example, solutions, syrups or suspensions, or they can be presented as a dry product for constitution with water or other suitable vehicle before use. Preparations for oral administration can be suitably formulated to give controlled release of the active compound.

IKK inhibitors can also be aerosolized or otherwise prepared for administration by inhalation. For example a fluorocarbon formulation and a metered dose inhaler, or inhaled as a lyophilized and milled powder. For administration by inhalation, the IKK inhibitors can be utilized in aerosol formulation to be administered via inhalation. The compounds of the present invention can be formulated into pressurized acceptable propellants such as dichlorodifluoromethane, propane, nitrogen and the like.

If an IKK inhibitor is coadministered with another IKK inhibitor, or with another agent having similar biological activity, the different active ingredients may be formulated together in an appropriate carrier vehicle to form a pharmaceutical composition. Alternatively, the IKK inhibitors can be formulated separately and administered simultaneously or in sequence.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

Methods of Treatment

Is some embodiments, an individual suffering from or at risk of HD is treated (including prevention) by administering a composition comprising one or more IKK inhibitors at a therapeutically effective dose. As discussed above, treatment can include an amelioration of the symptoms associated with the pathological condition afflicting the host, where amelioration is used in a broad sense to refer to at least a reduction in the magnitude of a parameter, e.g. symptom, associated with the pathological condition being treated, such as neuronal cell death. As such, treatment includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition. However, treatment can also be delay or slowing of disease progression, amelioration or palliation of the disease state, and remission (whether partial or total), whether detectable or undetectable.

A variety of individuals are treatable. Generally such individuals are mammals, where the term is used broadly to describe organisms which are within the class mammalia, including the orders carnivore (e.g., dogs and cats), rodentia (e.g., mice, guinea pigs, and rats), and primates (e.g., humans, chimpanzees, and monkeys). In preferred embodiments, the individuals are humans.

The IKK inhibitors may be administered using any convenient protocol capable of resulting in the desired therapeutic activity. A specific protocol can readily be determined by a skilled practitioner without undue experimentation based on the particular circumstances. Thus, the IKK inhibitor can be incorporated into a variety of formulations for therapeutic administration, as discussed above, depending on the protocol adapted by the supervising clinician.

Each dosage for human and animal subjects preferably contains a predetermined quantity of one or more IKK inhibitors calculated in an amount sufficient to produce the desired effect, in association with a pharmaceutically acceptable diluent, carrier or vehicle. Again, the actual dosage forms will depend on the particular compound employed, the effect to be achieved, and the pharmacodynamics associated with each compound in the host.

Administration of the IKK inhibitors can be achieved in various ways, including intracranial, for example injection directly into the brain tissue or into the cerebrospinal fluid, oral, buccal, rectal, parenteral, intraperitoneal, intradermal, transdermal, intracheal, intracerebral, etc., administration. The IKK inhibitors may be administered alone or in combination with one or more additional therapeutic agents. Administration "in combination with" one or more further therapeutic agents includes both simultaneous (at the same time) and consecutive administration in any order.

Administration may be chronic or intermittent, as deemed appropriate by the supervising practitioner, particularly in view of any change in the disease state or any undesirable side effects. "Chronic" administration refers to administration of the IKK inhibitor in a continuous manner while "intermittent" administration refers to treatment that is not done without interruption.

Combinations of IKK inhibitors for simultaneous administration are used in some embodiments. For example, two or more different IKK inhibitors may be administered in combination.

In a particular embodiment, IKK inhibitors of the invention are administered by intracranial injection. The injection will typically be directly into affected brain regions or into the cerebrospinal fluid.

An effective amount of an IKK inhibitor to be employed therapeutically will depend, for example, upon the therapeutic objectives, the route of administration, the nature of the IKK inhibitor, and the condition of the patient. Accordingly, it will be necessary for the therapist to titer the dosage and modify the route of administration as required to obtain the optimal therapeutic effect. A typical daily dosage might range from about 0.01 µg/kg to up to 1 mg/kg or more, depending on the factors mentioned above. Preferably, a typical daily dosage ranges from about 1 µg/kg to about 100 µg/kg. Typically, the clinician will administer an IKK inhibitor until a dosage is reached that provides the best clinical outcome. The progress of this therapy is easily monitored by conventional assays.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting large therapeutic indices are preferred. While compounds that exhibit toxic side effects can be used, care should be taken to design a delivery system that targets such compounds to the site of affected tissue in order to minimize undesired side effects.

Screening Assays for IKK Inhibitors

In other embodiments, therapeutics useful in treating HD are identified by screening for compounds that inhibit IKK activity. Screening assays are well known in the art and can readily be adapted to identify IKK inhibitors. As discussed above, such IKK inhibitors may include compounds that interact with (e.g., bind to) IKK, compounds that interfere with the interaction of IKK with its binding partners, cognate or substrate, and compounds that modulate IKK gene expression, such as compounds that modulate the level of IKKγ gene expression, or otherwise modulate the levels of IKK in the body. Assays may additionally be utilized which identify compounds that bind to IKK gene regulatory sequences (e.g., promoter sequences) and, consequently, may modulate IKK gene expression. See, Platt, K. A., 1994, *J. Biol. Chem.* 269: 28558-28562, which is incorporated herein by reference in its entirety.

The compounds which may be screened in accordance with the invention include, but are not limited to small molecules, peptides, antibodies and fragments thereof, and other organic compounds (e.g., peptidomimetics). The compounds may include, but are not limited to, soluble peptides, including members of random peptide libraries; (see, e.g., Lam, K. S. et al., 1991, *Nature* 354:82-84; Houghten, R. et al., 1991, *Nature* 354:84-86), and combinatorial chemistry-derived molecular libraries made of D- and/or L-configuration amino acids, phosphopeptides (including, but not limited to members of random or partially degenerate, directed phosphopeptide libraries; see, e.g., Songyang, Z. et al., 1993, *Cell* 72:767-778), antibodies (including, but not limited to, polyclonal, monoclonal, humanized, anti-idiotypic, chimeric or single chain antibodies, and FAb, F(abN)$_2$ and FAb expression library fragments, and epitope-binding fragments thereof), and small organic or inorganic molecules, including libraries thereof.

Other compounds which can be screened in accordance with the invention include, but are not limited to small organic molecules, including but not limited to those that are able to cross the blood-brain barrier.

Libraries of known compounds, including natural products or synthetic chemicals, and biologically active materials, including proteins, may be screened for compounds which are inhibitors of IKK. One method which detects protein interactions in vivo and can be used to identify IKK inhibitors, the two-hybrid system, is described in detail for illustration only and not by way of limitation. One version of this system has been described (Chien et al., 1991, *Proc. Natl. Acad. Sci. USA*, 88:9578-9582) and is commercially available from Clontech (Palo Alto, Calif.). The two-hybrid system may be adapted for screening for small molecule IKK inhibitors.

Briefly, in the two-hybrid system, plasmids are constructed that encode two hybrid proteins: one plasmid consists of nucleotides encoding the DNA-binding domain of a transcription activator protein fused to a nucleotide sequence encoding, for example, an IKK subunit, such as IKKγ, or a polypeptide, peptide, or fusion protein therefrom, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system may be adapted to screen for and identify small molecule IKK inhibitors that, for example, can disrupt the interaction of IKK subunits or the interaction of IKK and mutant Htt. By way of example, and not by way of limitation, an IKK yeast reporter strain can be generated by cotransforming a plasmid encoding an IKK subunit, such as IKKβ, gene product fused to a DNA-activation domain and a plasmid encoding a hybrid of an IKKγ gene product fused to the DNA-binding domain into a yeast reporter strain. The resulting IKK yeast reporter strain is useful for screening libraries, such as small molecule libraries, for IKK inhibitors. Small molecules capable of disrupting the IKK subunit interaction inhibit expression of the lacZ reporter.

The two-hybrid system or related methodology may also be used to screen activation domain libraries for proteins that interact with the "bait" gene product. By way of example, and not by way of limitation, an IKK subunit, such as IKKγ, can be used as the bait gene product. Total genomic or cDNA sequences are fused to the DNA encoding an activation domain. This library and a plasmid encoding a hybrid of a bait IKKγ gene product fused to the DNA-binding domain are cotransformed into a yeast reporter strain, and the resulting transformants are screened for those that express the reporter gene. For example, and not by way of limitation, a bait IKKγ gene sequence, e.g., the genes open reading frame, can be cloned into a vector such that it is translationally fused to the DNA encoding the DNA-binding domain of the GAL4 protein. The positive clones that display positive interaction are identified and the library plasmids responsible for reporter gene expression are isolated. DNA sequencing is then used to identify the proteins encoded by the library plasmids.

A cDNA library of the cell line from which proteins that interact with the bait IKKγ gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait IKKγ gene-GAL4 fusion plasmid into a yeast strain which contains a lacZ gene driven by a promoter which contains a GAL4 activation sequence. A cDNA encoded protein, fused to GAL4 transcriptional activation domain, that interacts with the bait IKKγ gene product will reconstitute an active GALA protein and thereby drive expression. Colonies which drive expression can be detected by methods routine in the art. The cDNA can then be purified from these strains, and used to produce and isolate the bait IKKγ gene-interacting protein using techniques routinely practiced in the art.

Small molecules may also have the ability to act as IKK inhibitors and thus may be screened for such activity. Small molecules preferably have a molecular weight of less than 10 kD, more preferably less than 5 kD and even more preferably less than 2 kD. Such small molecules may include naturally occurring small molecules, synthetic organic or inorganic compounds, peptides and peptide mimetics. However, small molecules in the present invention are not limited to these forms. Extensive libraries of small molecules are commercially available and a wide variety of assays are well known in the art to screen these molecules for the desired activity.

Candidate IKK inhibitor small molecules are preferably first identified in an assay that allows for the rapid identification of potential inhibitors. An example of such an assay is a binding assay wherein the ability of the candidate molecule to bind to IKK is measured. Such assays are well known in the art. Candidate molecules that are identified by their ability to bind to IKK may then be tested for their ability to inhibit one or more biological activities if IKK. This testing may include, for example, an immune complex kinase assay or gene reporter assay as described above. Compounds that appear to inhibit IKK activity can then be tested for their ability to prevent Htt mediated toxicity, preferably in a cell based assay, for example as described in Example 5 below. Compounds that are able to prevent or reduce Htt mediated toxicity are identified as therapeutics for treating HD.

Articles of Manufacture

In another aspect of the invention, articles of manufacture containing materials useful for the treatment of HD are provided. The articles of manufacture preferably comprise a container and a label or package insert on or associated with the container. Suitable containers include, for example, bottles, vials, syringes, etc. The containers may be formed from a variety of materials such as glass or plastic. The container holds a composition which is effective for treating HD and may have a sterile access port (for example the container may be an intravenous solution bag or a vial having a stopper pierceable by a hypodermic injection needle). At least one active agent in the composition is an IKK inhibitor. The label or package insert indicates that the composition is used for treating HD or a related disorder. In addition, the label or package insert may indicate that the patient to be treated is one who suffers from, or is likely to suffer from or develop Huntington's disease or a related disorder.

Alternatively, or additionally, the article of manufacture may further comprise a second (or third) container comprising one or more of another therapeutic agent, and a pharmaceutically-acceptable buffer, such as bacteriostatic water for injection (BWFI), phosphate-buffered saline, Ringer's solution or dextrose solution. It may further include other materials desirable from a commercial end user standpoint, including other buffers, diluents, filters, needles, and syringes.

EXAMPLES

The following examples, including the experiments conducted and results achieved are provided for illustrative purposes only and are not to be construed as limiting upon the present invention.

As demonstrated in the Examples below, mutant Htt can bind IKKγ, activate the IKK complex, and elevate NF-κB-dependent gene expression. Toxicity associated with this mutant Htt activity can be significantly reduced by inhibition of IKK activity.

Example 1 demonstrates that cultured cells expressing mutant Htt and striatal cells from HD transgenic mice have elevated NF-κB activity. Furthermore, NF-κB was found to be concentrated in the nucleus of neurons in the brains of HD transgenic mice. Mutant Htt was found to activate the IKK complex both in cell culture and in mouse models of HD (FIG. 3), as shown in Example 2. Example 3 demonstrates that activation of IKK is mediated by direct interaction with mutant Htt. In particular, the expanded polyglutamine stretch and adjacent proline-rich motifs in mutant Htt interact with IKKγ, a regulatory subunit of IKK. Optimal HDx1 binding to the IKK complex was found to require interaction with the first N-terminal 134 amino acids of IKKγ (FIG. 4), a domain that is essential for interaction with IKKβ and IKKα, two catalytic units of the IKK complex (May et al., *Science* 289: 1550-1554 (2000)). Interaction of Htt with IKKγ required polyQ expansion as well as the proline-rich motifs of HDx1.

As shown in Example 4, activation of IKK was found to mediate the toxicity of mutant Htt. Expression of IKKγ promoted aggregation and nuclear localization of mutant Htt exon-1. Moreover, in acute striatal slice cultures, inhibition of IKK activity with an N-terminally truncated form of IKKγ, which interferes with IKK activity, blocked mutant Htt-induced toxicity in medium-sized spiny neurons (MSNs). In addition, blocking degradation of NF-κB inhibitors with a dominant-negative ubiquitin ligase β-transducin repeat-containing protein also reduced the toxicity of mutant Htt in MSNs.

Example 1

Mutant Htt Activates the NF-κB Pathway

This example illustrates activation of the NF-κB pathway by mutant Htt.

Materials and Methods

Cells and transgenic animals. PC12 cells, which express wild-type (WT) HDx1-enhanced green fluorescent protein (EGFP) with 25 glutamine repeats (25Qs) or mutant HDx1-EGFP with 103Qs in response to ecdysone, were kindly provided by Dr. E. Schweitzer (University of California Los Angeles). These cells were cultured on a collagen I substrate (Fisher Scientific, Tustin, Calif.) in DMEM with 5% horse serum, 5% fetal bovine serum, 2 mM glutamine, and standard penicillin-streptomycin antibiotics. Immortalized striatal cells from WT and HD KI mice, provided by Dr. M. E. MacDonald, were cultured as described (Gines et al., 2003). Human embryonic kidney (HEK)-293 cells were cultured as described previously (Khoshnan et al., 2002). The HD transgenic mouse line R6/2 and a knock-in line, in which a 155 polyglutamine stretch was inserted in HDx1 of mouse Htt, have been described (Davies et al., 1997; Lin et al., 2001). Colonies were established and maintained in an animal facility.

Gene Reporter and transfections. The pNF-κB-luciferase with five enhanced elements and the control plasmid without NF-κB binding sites, pCIS-CK luciferase, were used for gene reporter assays (Strategene, La Jolla, Calif.). To normalize for transfection efficiency between samples, a β-galactosidase (β-gal) construct expressed from the EF-1α promoter (Invitrogen, Carlsbad, Calif.), was included in all gene reporter assays. PC12 cells were transfected with control or NF-κB-luciferase plasmids using lipofectamine-plus. On the following day, cells were left untreated or stimulated for 8 hr with 1 μg/ml ecdysone to induce expression of HDx1. Mock or NGF (Signa, St. Louis, Mo.) was added (50 ng/ml) and incubated for an additional 6 hr. Cells were suspended in lysis buffer on ice for 10 min and cleared by centrifugation. Luciferase activity was measured by addition of the substrate (Promega, Madison, Wis.) to equal amounts of protein from each sample. Striatal cells form WT and HD KI mice were transfected with an NF-κB reporter plus β-gal and anti-polyQ (MW2) or anti-polyproline [anti-polyP (MW7)] recombinant intrabodies (Khoshnan et al., 2002). On the following day, cells were starved for 2 hr and treated with 5 ng/ml recombinant IL-1β (R&D Systems, Minneapolis, Minn.) and incubated for an additional 6 hr. Cells were harvested and cleared lysate was used to measure luciferase as described above. All gene reporter assays were corrected for transfection efficiency by normalizing the units if β-gal in the extracts, using the β-gal assay (Invitrogen). β-gal values from the samples were divided by the β-gal value from control, 25polyQ, non-induced PC12 cells (no expression of HDx1) and multiplied by each corresponding luciferase reading. For striatal cells, β-gal values were divided by the value obtained for Wt cells without any treatment. Results are shown as relative luciferase units and are representative of at least three independent experiments. Data points are the average of triplicate measurements.

Immunohistochemistry of tissue sections. Brains were taken from paraformaldehyde-fixed WT and R6/2 HD transgenic mice, and cryosections were permeabilized in 70% methanol for 1 hr at −20° C. After blocking in 3% BSA and 10% normal goat serum, slides were incubated with anti-p65 (Santa Cruz Biotechnology, Santa Cruz, Calif.) and the neuronal marker anti-neuronal-specific nuclear protein (NeuN) antibodies (Chemicon), p65-positive cells were detected with a goat anti-rabbit secondary antibody conjugated to FITC and goat anti-mouse Alexa Fluor 594 (Molecular Probes). Toto-3 was used to stain nuclei. Sections were examined with a confocal microscope. Total neurons from 16 coronal sections containing cortical and striatal areas of four animals each of WT and HD mice were quantified, and the average percentage of cells with nuclear p65 is presented.

Results

1. Induction of Mutant HDx1 Expression Increases Transcription from the NF-κB-Dependent Promoter Approximately Fivefold Over that of Noninduced Cells.

To assess the ability of mutant Htt to activate the NF-κB pathway, PC12 cells that express WT (25Q) or mutant (103Q) HDx1 in response to ecdysone were used (FIG. 1A). These cells were transfected with a reporter construct containing NF-κB enhancer element whose activation is read out as luciferase activity. The inducible nature of HDx1 expression allows the examination of soluble mutant HDx1 function, before macro-aggregates become visible. Induction of mutant HDx1 expression increases transcription from the NF-κB-dependent promoter approximately fivefold over that of noninduced cells, whereas WT HDx1 has minimal effect (FIG. 1A). These results are consistent with a recent report demonstrating upregulation of NF-κB expression by mutant HDx1 in inducible PC12 cells (Sugars et al., 2004).

2. Mutant Htt Influences Signal-Induced NF-κB Activation.

To examine whether mutant HDx1 also influences signal-induced NF-κB activation, NGF, which is known to activate NF-κB in PC12 cells, was used (Foehr et al., 2000). Mutant (but not WT) HDx1 strongly enhances NGF-induced NF-κB dependent gene expression (FIG. 1A). Because mutant Htt has been shown to variably influence gene expression from different promoters, the same experiment was performed with a control plasmid that lacks an NF-κB enhancer element. Expression of WT or mutant HDx1 does not influence luciferase expression from the control plasmid (FIG. 1B), suggesting that the elevated NF-κB values in FIG. 1A are mediated by mutant HDx1 expression. Under the conditions tested, most of the HDx1 remains in the detergent-soluble fraction and is detectable by Western blotting (FIG. 1A); however, the NF-κB activity diminishes as mutant HDx1 accumulates and aggregates (data not shown). Thus, soluble mutant HDx1 activates endogenous, and augments NGF-induced, NF-κB dependent gene expression. Moreover, expression of mutant HDx1 promotes degradation of the inhibitory protein Iκ-Bα, a hallmark of NF-κB activation. Levels of IκBα drop significantly by 3 hr and return to normal by 7 hr after induction (FIG. 1C). These data confirm the gene reporter assay results and suggest that mutant Htt-induced NF-κB is mediated by degradation of Iκ-Bα.

3. Mutant Htt Influences NF-κB Activity.

To examine whether full-length mutant Htt also influences NF-κB activity, immortalized striatal cell lines obtained from WT and HD KI mice were used (Gines et al., 2003). Using the reporter with NF-κB enhancer, no significant difference in basal NF-κB activity is observed between striatal cells from WT and HD KI mice (FIG. 1D) (compare C values in WT and mutant). These data are consistent with a recent report showing that inducible expression of full-length WT or mutant Htt in PC12 cells has no effect on basal NF-κB activation (Sugars et al., 2004). Thus it was investigated whether WT and mutant cells respond differently to NF-κB inducing agents. KI striatal cells display a stronger response than WT cells to the NF-κB-inducing cytokine IL-1β (FIG. 1D).

4. Mutant Htt Mediates the Enhanced Response to IL-1β.

Recombinant single chain intrabodies, which are known to interfere with the function of mutant HDx1 (Khoshnan et al., 2002) were used to verify that mutant Htt mediates the enhanced response to IL-1β. Two intrabodies, MW2 targeting the expanded polyQ and MW7 recognizing the polyP motifs of HDx1, reduce the IL-1β-mediated NF-κB activation in stiratal cells from KI mice (FIG. 1D). MW7 is somewhat more potent than MW2 at inhibiting the effects of full-length mutant Htt on NF-κB.

Activated NF-κB functions primarily in the nucleus, where it regulates gene expression. To confirm the authenticity of the gene reporter assays, nuclear p65 binding to a consensus NF-κB oligonucleotides was measured. Extracts from mutant Htt KI striatal cells show elevated nuclear p65 binding in response to IL-1β treatment when compared with the equivalent samples from WT striatal cells (FIG. 2A). Specificity of binding was confirmed using a mutated consensus NF-κB oligonucleotide, which failed to show p65 binding in this assay (data not shown). Thus, cells expressing full-length mutant Htt respond more vigorously than cells with WT Htt to IL-1β-induced NF-κB nuclear localization.

5. Mutant Htt Promotes Nuclear Localization of NF-κB In Vivo.

Brain sections from 8-week-old R6/2 HD mice and age-matched controls were stained with an antibody that recognizes the p65 subunit. p65 is concentrated in the nucleus of a majority of the NeuN-positive neurons in the cortex and striatum of HD mice, whereas most of the neurons of the age-matched WT mice contain cytoplasmic p65 (FIG. 2 B, C). Thus, mutant Htt promotes nuclear localization of NF-κB in vivo as well as in cell culture.

Example 2

Mutant Htt Activates the IKK Complex

This example illustrates the activation of the IKK kinase pathway by mutant Htt.

Materials and Methods

For coimmunoprecipitation studies, PC12 cells or striatal tissue of WT and HD transgenic mice was lysed by sonication in buffer A (50 mM HEPES, pH 7.6, 250 mM NaCl, 1% Triton X-100, 2 mM $MgCl_2$, mM DTT, 1 mM $Na_3VO_4$, and 20 μm β-glycerophosphate) and a mixture of protease inhibitors (Boehringer Mannheim, Mannheim, Germany). Equal amounts of cleared extracts from each sample were incubated with a rabbit anti-IKKγ (Santa Cruz Biotechnology) coupled to protein-A beads and rocked for 3 hr at 4° C. Cells were washed five times with buffer A. Immune complexes were examined by SDS-PAGE followed by Western blotting with monoclonal antibodies targeting Htt (Kop et al., 2001), as described in the figure legends.

Immune complex kinase assays. To measure IKK activity, immunoprecipitated IKK complexes were examined for the ability to phosphorylate GST-IκBα in vitro. The construct for the N-terminal 61 amino acids of GST-IκBα, which contains the IKK phosphorylation sites (provided by Dr. W. Greene, University of California San Francisco), was expressed in *E. coli* and purified on glutathione beads as described in the manufacturer's instructions (Amersham Biosciences). To obtain IKK complexes, equal amounts of cleared striatal extracts from WT and HD animals, or from PC12 cells induced to express WT or mutant HDx1-EGFP (all in buffer A), were incubated with a mouse anti-IKKα antibody (Santa Cruz Biotechnology) coupled to protein-A beads and rocked for 3 hr at 4° C. Beads were washed five times in buffer B (50 mM HEPES, pH 7.6, 250 mM NaCl, 1 M urea, 0.1% Nonidet P-40, 6 mM EDTA, 6 mM EGTA, 1 mM DTT with 20 μM β-glycerophosphate) and a mixture of protease inhibitors and equilibrated in kinase buffer (20 mM HEPES, pH 7.6, 2 mM $MgCl_2$, 2 mM $MnCl_2$, 10 μM ATP, 10 mM glycerophosphate, 10 mM NaF, 200 μM $Na_3VO_4$, 1 mM dithiothreitol DTT). IKK activity was evaluated in vitro with 1 μg of purified GST-IκBα (N-terminal 61 amino acids) in the presence of 10 μCi of [$^{32}$P]γ-ATP for 30 min at 30° C. Products were examined by SDS-PAGE followed by autoradiography. Duplicate samples were examined by Western blotting using a rabbit anti-IKKγ antibody (Santa Cruz Biotechnology).

Results

1. The IKK Complex is Activated by Mutant HDx1 Expression.

Signal-induced phosphorylation of serine residues 32 and 36 of IκBα, which is mediated by the IKK complex, is essential for the ubiquitination and proteosome-mediated degradatin of IκBα (Ghosh and Karin, 2002). Immunoprecipitated endogenous IKK complexes from extracts of control or PC12 cells induced to express mutant HDx1 were analyzed for their kinase activity by measuring phosphorylation of the recombinant substrate, GST-IκBα. The kinase activity of IKK from cells expressing mutual HDx1 is significantly higher than that from non-HDx1-induced cells (FIG. 3A). As expected, NGF treatment also activates the IKK complex, and consistent with the gene reporter assay results, kinase activity appears to be elevated somewhat further when both NGF and HDx1 are present (4.1-fold compared with a 2.4- and 3.2-fold in the ecdysone and NGF-treated cells, respectively). Expression of WT HDx1 has no effect on IKK activity (not shown).

2. IKK Activation by Mutant HDx1 Occurs In Vivo.

Two lines of HD transgenic mice, R6/2 (Davies et al., 1997) and a mutant Htt KI (Lin et al., 2001) were used to investigate whether IKK activation by mutant HDx1 also occurs in vivo. IKK complexes immunoprecipitated from striatal or cortical extracts of WT and HD mice were assayed in vitro for IKK activity. Consistent with the PC12 cell results, IKK activity is higher in complexes isolated from striatal (9-fold) as well as cortical (3.8-fold) extracts of 2-month-old R6/2 mice compared with age-matched WT controls (FIG. 3B). With KI HD mice, a significant increase in IKK activity is detected in the striatum at 1 year of age (4.8-fold higher than WT) (FIG. 3C).

3. HDx1 Associates with IKK.

Complexes isolated with an anti-IKK antibody from PC12 cells were examined for the presence of HDx1 by Western blotting. Soluble mutant HDx1 coprecipitates with IKK, whereas minimal WT HDx1 is observed (FIG. 3D). Thus, IKK physically forms a complex with mutant HDx1. This interaction also occurs in the brain of HD mice. IKK complexes isolated from brain extracts of R6/2 mice contain soluble HDx1, which is recognized by anti-Htt antibody (FIG. 3E).

Example 3

Mutant Htt Interacts with IKKγ

This example illustrates the interaction of mutant Htt with IKKγ.

Materials and Methods

Protein-protein interaction. In vitro binding of IKKγ to mutant HDx1 was performed using glutathione S-transferase (GST)-pull down assays. GST-HDx1 with 20 or 51 polyQs, with and without polyproline domains, was obtained from Dr. E. Wanker (Max Plank Institute, Berlin, Germany). These constructs were expressed in *Escherichia coli* and purified with glutathione beads (Amersham Biosciences, Piscataway, N.J.) according to manufacturer's instructions. IKKγ constructs were transcribed and translated in rabbit reticulocytes in the presence of [$^{35}$S] methionine (Promega). Briefly, 5 μg of GST-HDx1 bound to beads was incubated with 10 μl of each labeled in vitro-translated IKKγ produce in 500 μl of Tris-based buffer containing 10% glycerol and 6 mM DTT and rocked at room temperature for 2 hr. Beads were washed five times in the same buffer. Bound IKKγ was examined by SDS-PAGE, followed by autoradiography. Recombinant anti-HDx1 intrabodies (Khoshnan et al., 2002) were expressed and examined similarly from binding to GST-HDx1. For competition assays, 10-fold excess in vitro-translated intrabodies were added to GST-HDx1 plus deleted C terminus IKKγ and processed as above.

Results

1. The Binding of Mutant HDx1 to the IKK Complex is Mediated by IKKγ.

Figure 4C:
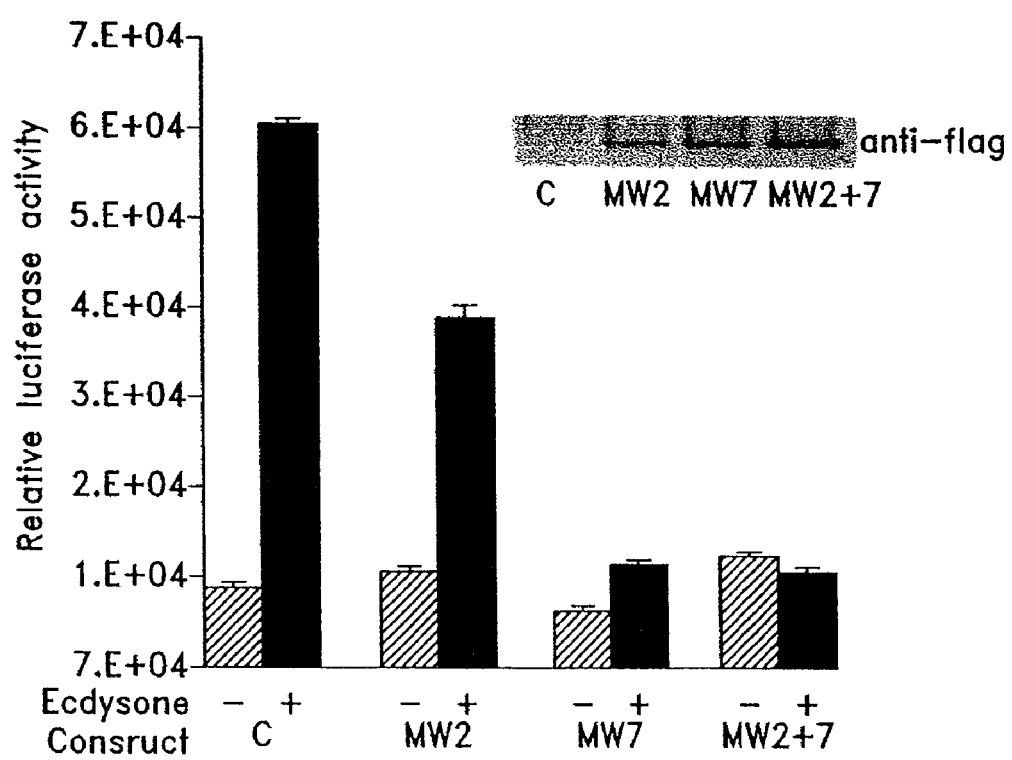
FIG. 4 shows mutant Htt directly interacts with IKKγ. A, shows several gells demonstrating that full-length (F) and C-terminal-truncated IKKγ (DC) bind to mutant HDx1 (51polyQ). B, shows a gel confirming that binding of IKKγ to mutant HDx1 requires the Htt polyQ and polyP domains. C, is a graph illustrating that expression of anti-HDx1 recombinant antibodies, which block binding of IKKγ to Htt, reduces NF-κB-dependent gene expression.

The activity of the IKK complex is regulated by IKKγ, a glutamine-rich nonkinase subunit of the complex (Rothwarf et al., 1998); Ghosh and Karin, 2002). A homolog of IKKγ that participates in tumor necrosis factor-α receptor signaling interacts with Htt in a yeast two-hybrid assay (Hattula and Paranen, 2000). A GST pull-down assay using HDx1 fused to GST and [$^{35}$S] methionine-labeled IKKγ was used to determine whether the binding of mutant HDx1 to the IKK complex is mediated by IKKγ. The stringency of the assay was such that there was no binding to GST alone. In vitro translated-IKKγ preferentially binds to GST-HDx1 containing expanded polyQ (FIG. 4A). Although deletion of the C-terminal 119 amino acids of IKKγ (DC-IKKγ) has no apparent effect on this binding, removal of the first 134 amino acids (DN-IKKγ) diminishes binding to HDx1 (FIG. 4A). Interestingly, mutant HDx1 without its polyP domains does not bind efficiently to Ikkγ (FIG. 4B). Although it is not possible to rule out that the absence of proline may also the solubility of mutant HDx1 and thus artifactually reduce binding to IKKγ, the importance of the polyP domains is further supported by antibody experiments. Competition assays using in vitro-translated, anti-Htt recombinant intrabodies have been performed (Khoshnan et al., 2002). Coincubation of DC-IKKγ plus mutant HDx1 with 10-fold excess of intrabodies specific for polyQ (MW2) or polyP (MW7) competes with binding of IKKγ to HDx1 (FIG. 4B). Moreover, these intrabodies inhibit the HDx1-induced NF-κB-dependent gene expression in PC12 cells (FIG. 4C). Although anti-polyQ intrabody has a modest inhibitory effect, anti-polyP (MW7) significantly minimizes mutant HDx1-induced NF-κB activation. Thus, IKKγ binding to mutant HDx1 requires the polyQ expansion and is influenced by the polyP domains.

Example 4

Inhibition of the NF-kB Pathway Reduces HDx1-Induced Toxicity in Cell Culture and Brain Slices This example illustrates the protection against mutant Htt toxicity in MSNs by inhibition of the NFκB pathway.

Materials and Methods

Gene Reporter and transfections. To examine the effects of ΔF-βTrCP (obtained from Dr. R. Deshaies (California Institute of Technology) and originally provided by Spencer et al. (1999)) and deleted N terminus (DN)-IKKγ on mutant HDx1-induced NF-κB, PC12 cells were transfected with ΔF-βTrCP or DN-IKKγ plus β-gal and NF-κB reporter in six-well plates. Induction of HDx1 with ecdysone and NGF treatment was as described above. Equal amounts of each sample were used to measure luciferase activity. Binding of NF-κB to its consensus oligonucleotide site was assayed in striatal neurons with the BD TransFactor Kit specific for the p65 subunit following the manufacturer's instructions (BD Biosciences, Mountain View, Calif.). Briefly, striatal cell lines from WT and HD K1 mice were starved for 2 hr and treated with 6 ng/ml IL-1β for 15 or 30 min. Nuclear extracts were obtained using commercial reagents (BD Biosciences). Protein concentration was determined by the BCA method (Pierce, Rockford, Ill.). Equal amounts of each nuclear fraction were added to wells coated with an NF-κB consensus or mutated control oligonucleotide and incubated at room temperature for 1 hr. Wells were washed extensively and incubated with primary rabbit antibody specific for the p65 subunit of NF-κB. Bound p65 was detected with a goat anti-rabbit antibody conjugated to horseradish peroxidase. After addition of the substrate 3,3-5,5-tetramethylbenzidine, color development was measured at 655 nm using an ELISA plate reader. Samples were done in triplicate, and the results shown are representative of three independent experiments.

Transfection of HEK-293 cells with mutant HDx1-EGFP alone (Kasantsev et al., 1999) or with one of the following constructs, full-length (F), DN, and deleted C terminus (DC) of IKKγ (provided by Dr. E. Zandi, University of Southern California) Rothwarf et al., 1998) or ΔF-βTrCP, was done using lipofectamine-plus reagents (Invitrogen). For histochemistry, cultured cells were fixed in 4% paraformaldehyde for 30 min, permeabilized with 70% methanol for 1 hr., and washed with PBS. Cells were stained with anti-HA for IKKγ or anti-myc for ΔF-βTrCP (Cell Signaling, Beverly, Mass.) followed by a goat anti-mouse antibody conjugated by Alexa 594 (Molecular Probes, Eugene, Oreg.). Toto-3, a dimeric cyanine, was used to stain nuclei (Molecular Probes). Cells were washed in PBS, mounted on microscope slides, and examined with a confocal microscope. Mutant HDx1 toxicity was assessed by counting the number of condensed GFP-positive bodies, which are remnants of terminated deoxynucleotidyl transferase-mediated biotinylated UTP nick endlabeling (TUNEL)-positive (TUNEL$^+$) cells (Khoshnan et al., 2002), using a florescence microscope. For TUNEL staining, transfected cells grown on coverslips were air dried and fixed 16 hr after transfection as above and permeabilized in ethanol/acetic acid (2:1). Apoptotic cells were labeled with terminal deoxynucleotidyl transferase using digoxigenin-labeled nucleotides and detected by anti-digoxigenin antibody and rhodamine-conjugated secondary according to the instructions provided by the manufacturer (Chemicon, Temecula, Calif.).

Brain slice preparation. All animal experiments were performed in accordance with the Institutional Animal Care and Use Committee and Duke University Medical Center Animal Guidelines. Postnatal day 7 (P7) CD Sprague Dawley rats (Charles River Laboratory, Raleigh, N.C.) were decapitated, and the brains were surgically removed and placed in ice-cold Neurobasal medium (Invitrogen). The tissue was fixed to a chilled, stainless steel Vibratome stage using cyanoacrylate glue (Krazy-Glue) and covered with Neurobasal medium. Coronal brain slices (250 μm thick) were cut by Vibratome (VT1000S; Leica, Nusslock Germany) as described previously (Edgerton and Reinhart, 2003). Brain slices were kept at 37° C. in 5.0% $CO_2$ for 1 hr.

Bolistic transfection. Gold particles (1.6 μm gold microcarriers; BioRad, Hercules, Calif.) were used as DNA carriers for transfection as described previously (Lo et al., 1994). Briefly, gold particles were sonicated in 0.05 M spermidine in the presence of plasmid DNA. The gold-DNA mixture was washed three times in 100% ethanol before being loaded into Helios plastic cartridges (Bio-Rad) according to manufacturer's instructions. Slices were transfected using a Bio-Rad Helios gun with a cyan fluorescent protein (CFP)-tagged Htt fragment, together with yellow fluorescent protein (YFP) as a morphometric marker. In a number of experiments, one of the IKKγ constructs was also cotransfected with the Htt-construct and YFP. CFP-tagged Htt fragments were exon-1-N-terminal fragments containing either a short-Q (Q23) or a long-Q (Q148) polyQ domain.

Brain slice neurodegeneration assay. For each condition, transfections were performed on twelve brain slices per experiment. Protein expression and neurodegeneration (loss of processes, shriveling of the soma) were assay 2-7 d after transfection using a Leica fluorescence microscope with appropriate filters for YFP and CFP. The total area of the striatum was identified, and transfected MSNs were identified by their morphology. CFP fluorescence was used to determine expression of Htt fragments and their aggregation into macro-inclusions. Each experiment involved three to twelve transfected brain slices per condition, and the data are means from six independent experiments for each condition.

Results

1. IKKγ can Modify the Toxicity of Mutant HDx1.

Figure 5A:
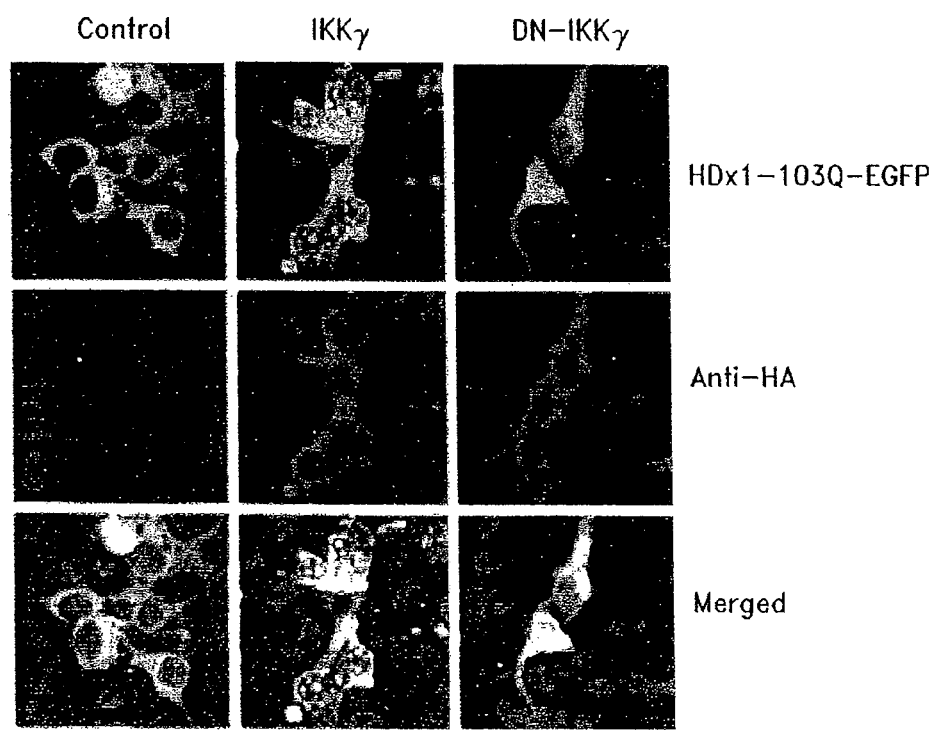
FIG. 5 shows DN-IKKγ reduces the toxicity of mutant HDx1. A, IKKγ promotes aggregation and nuclear localization of Htt. B, DN-IKKγ expression reduces the toxicity of mutant HDx1. C, is a graph illustrating that DN-IKKγ blocks HDx1-induced NF-κB activation.
Figure 5B:
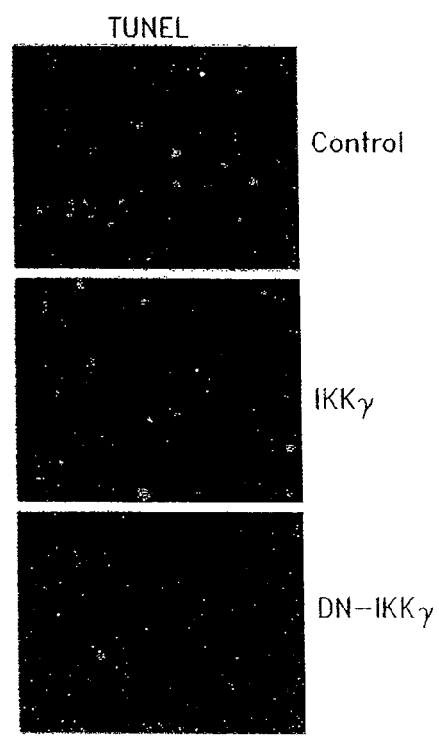
Figure 5C:
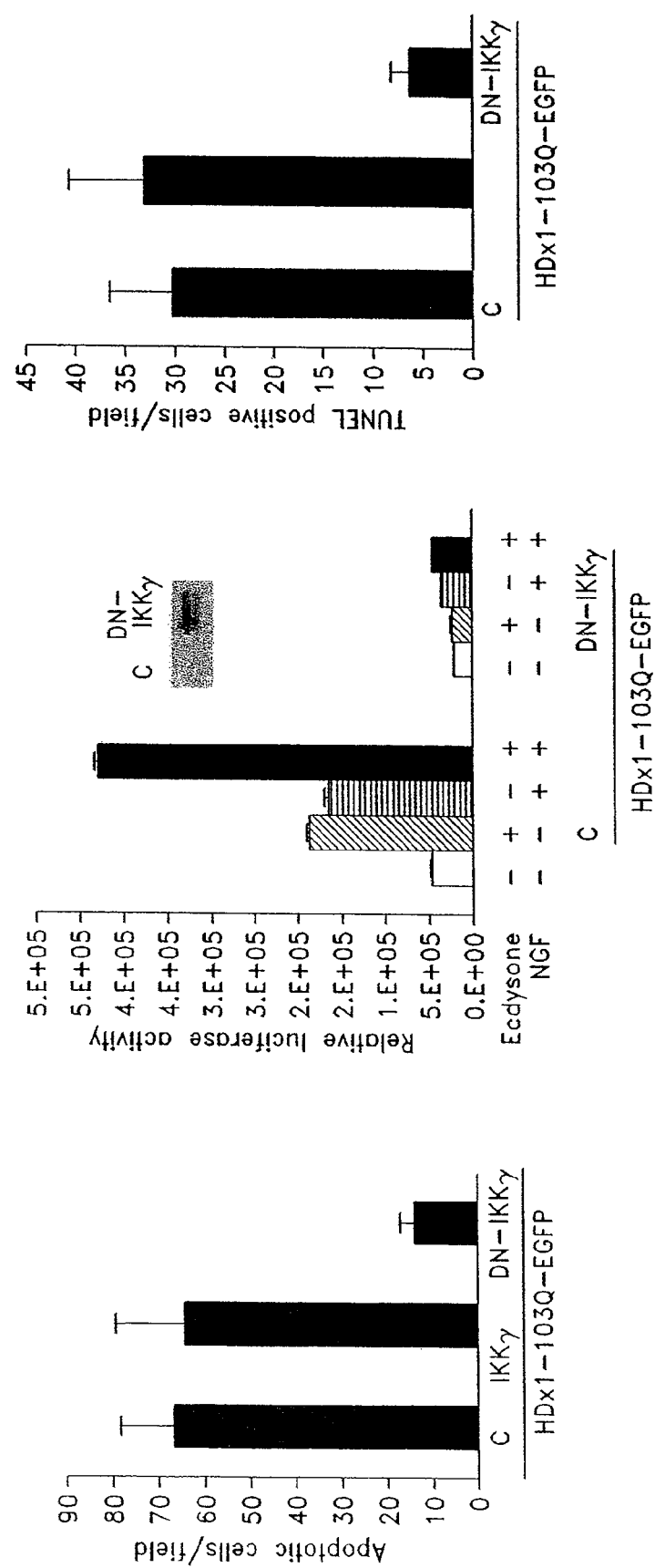

Confocal microscope examination of HEK-293 cells expressing mutant HDx1 and IKKγ at an early time point before widespread toxicity shows that full-length IKKγ promotes aggregation of mutant HDx1 (FIG. 5A). Intracellular, microscopically visible aggregates are apparent, and importantly, some of these aggregates localize in the nucleus of transfected cells. C-terminally truncated IKKγ, which also binds to mutant HDx1 (FIG. 4A), has a similar effect (data not shown). On the other hand, DN-IKKγ, which does not bind to mutant HDx1, has no apparent effect on HDx1 aggregation (FIG. 5A). Thus, binding to IKKγ appears to have little effect on toxicity at 48 hr after transfection, however, because the overall number of cells killed by mutant HDx1 does not appear to change (FIG. 5A). Toxicity was assessed by counting the number of condensed GFP$^+$ bodies at 48 hr after transfection, which are remnants of dead cells (Khoshnan et al., 2002) (see FIG. 7B). Importantly, DN-IKKγ strongly reduces the toxicity of mutant HDx1 (FIG. 5A, graph). The effect of DN-IKKγ on mutant HDx1 toxicity was confirmed by TUNEL assay. Compared with cultures with or without full IKKγ, the number of TUNEL$^+$ cells is significantly reduced in cells cotransfected with DN-IKKγ and mutant HDx1 (FIG. 5B). DN-IKKγ lacks the binding domain essential for interaction with IKKα and -β and interferences with IKK activity (May et al., 2000; Poyet et al., 2000). DN-IKKγ also blocks basal and NGF-induced NF-κB-dependent gene expression by mutant HDx1 in inducible PC12 cells (FIG. 5C). Therefore, inhibition of mutant HDx1 toxicity by DN-IKKγ may be mediated through blockage of NF-κB pathway.

2. DN-IKKγ Reduces the Neurotoxicity of Mutant HDx1 In Vivo.

Figure 6A:
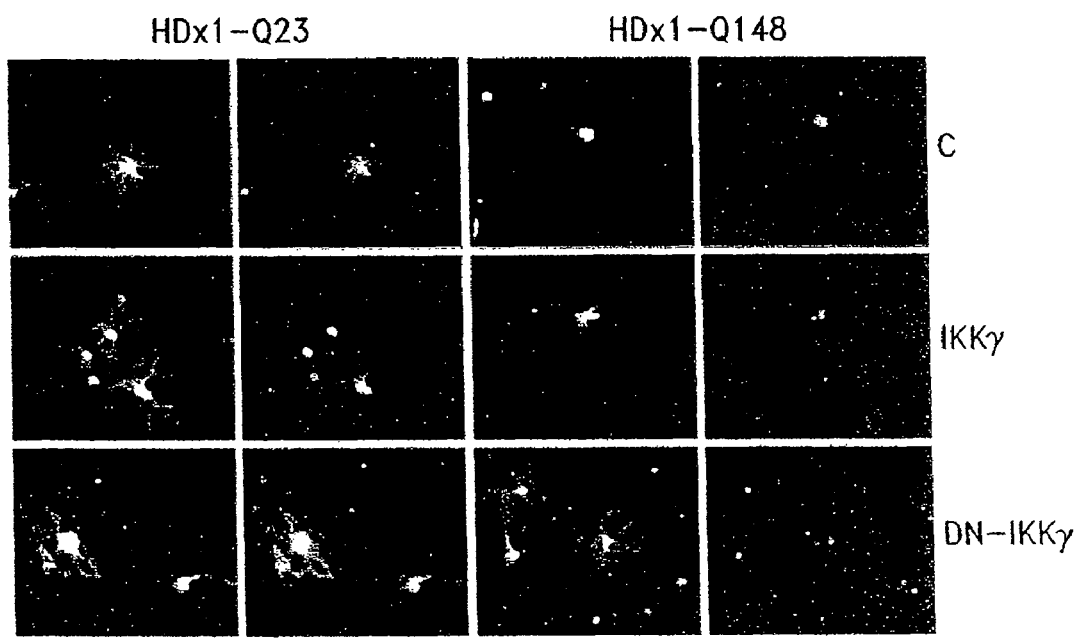
FIG. 6 shows DN-IKKγ protects striatal MSNs against mutant HDx1. A, is a series of micrographs showing that living MSNs can be monitored for morphology and Htt expression. B, is a graph illustrating that expression of DN-IKKγ is neuroprotective for MSNs in brain slices.
Figure 6B:
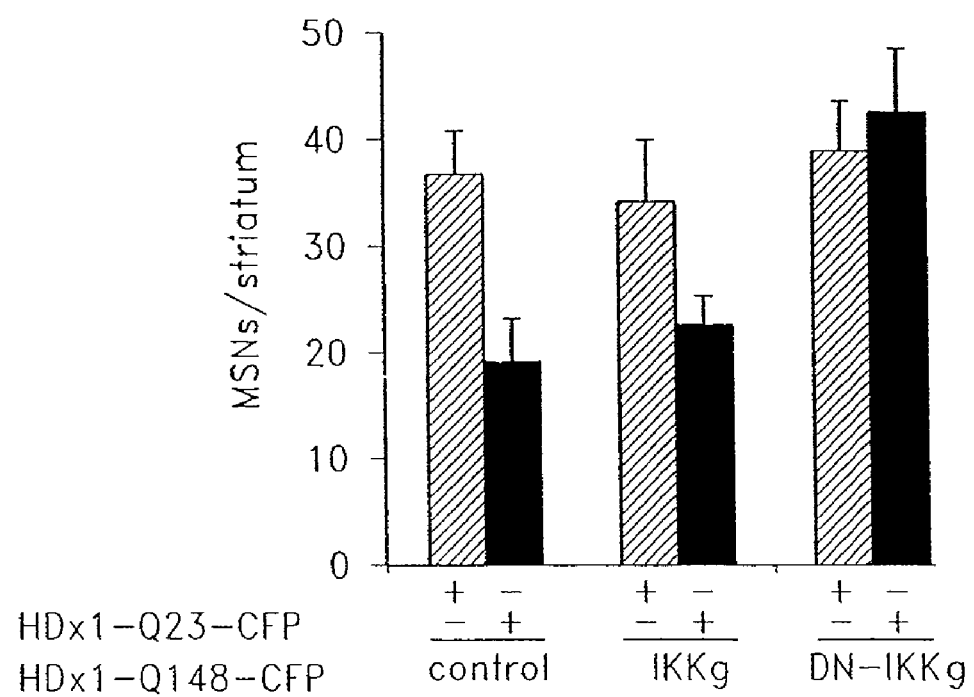

A novel, acute, P7 rat brain slice assay was used to assess the effects of IKKγ in vivo. A biolistic method is used to cotransfect neurons with three constructs HDx1-CFP to visualize HDx1 expression and associated neurodegeneration, YFP to monitor the full morphology of transfected cells, and IKKγ or DN-IKKγ. Individual transfected MSNs are identified by location and morphology and monitored daily for 7 d after transfection. Neuronal viability was quantified by counting the number of $CFP^+$ neurons in each slide at 7 d. Expression of mutant HDx1 after transfection and to cell death within 4-7 d. YFP apoptotic bodies are seen initially, followed by complete loss of YFP fluorescence. In contrast, neurons transfected with WT HDx1 do not contain Htt inclusions and retain their normal dendritic structure (FIG. 6A). Coexpression of full-length IKKγ or DN-IKKγ has no obvious effect on MSNs expressing WT HDx1 (FIG. 6A, B). Furthermore, expression of IKKγ has no significant effect on neurodegeneration induced by expression of mutant HDx1 (FIG. 6A, B); however, the coexpression of DN-IKKγ with mutant HDx1 is significantly neuroprotective (FIG. 6A, B). The neuroprotective function of DN-IKKγ is essentially independent of aggregate formation by mutant Htt, because rescued neurons still contain Htt macro-aggregates (FIG. 6A). These brain slice results indicate that DN-IKKγ also reduces the neurotoxicity of mutant HDx1 in MSNs residing in a more intact, three-dimensional setting.

3. Blocking Degradation of Iκ-B can Reduce the Toxicity of Mutant HDx1.

Figure 7B:
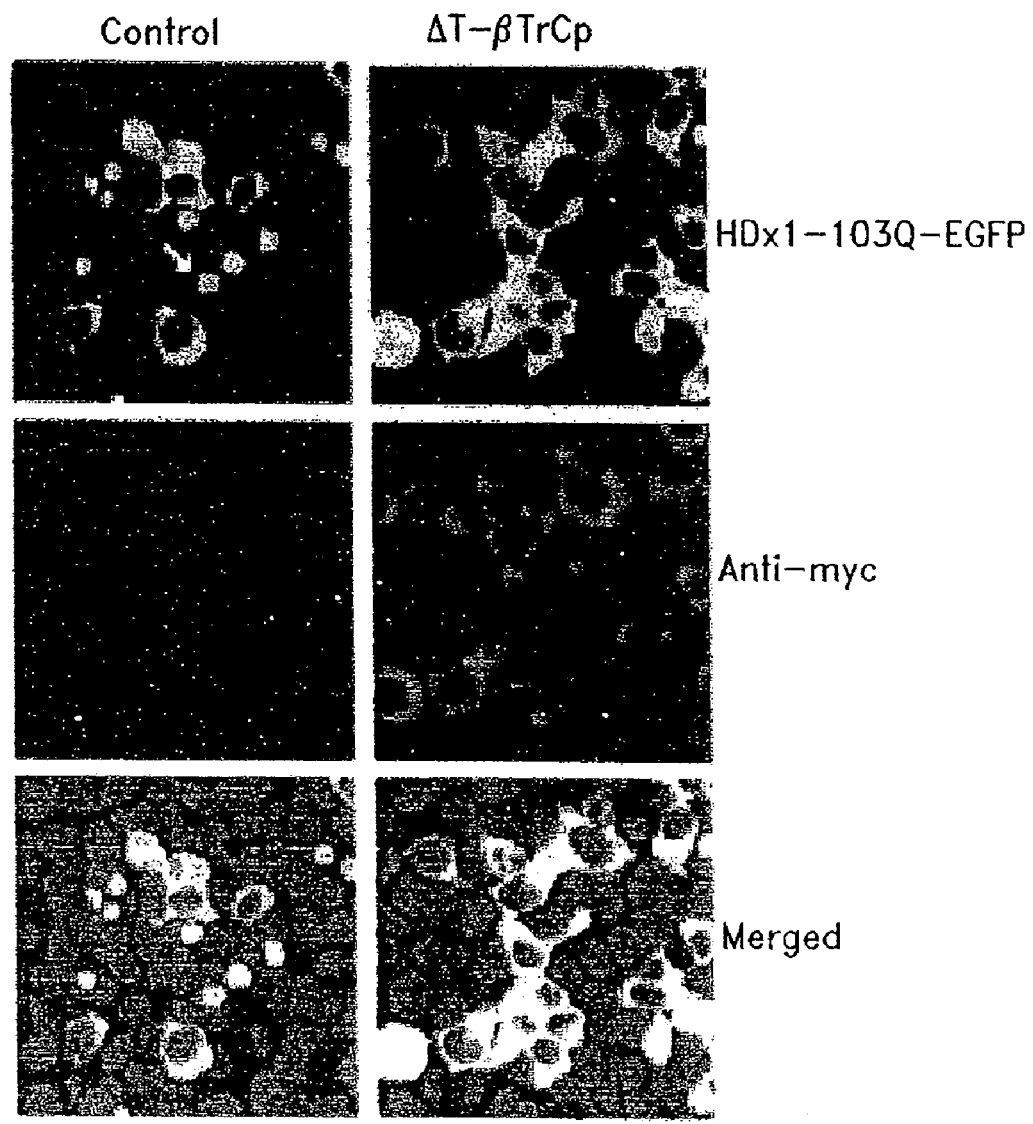
Figure 7D:
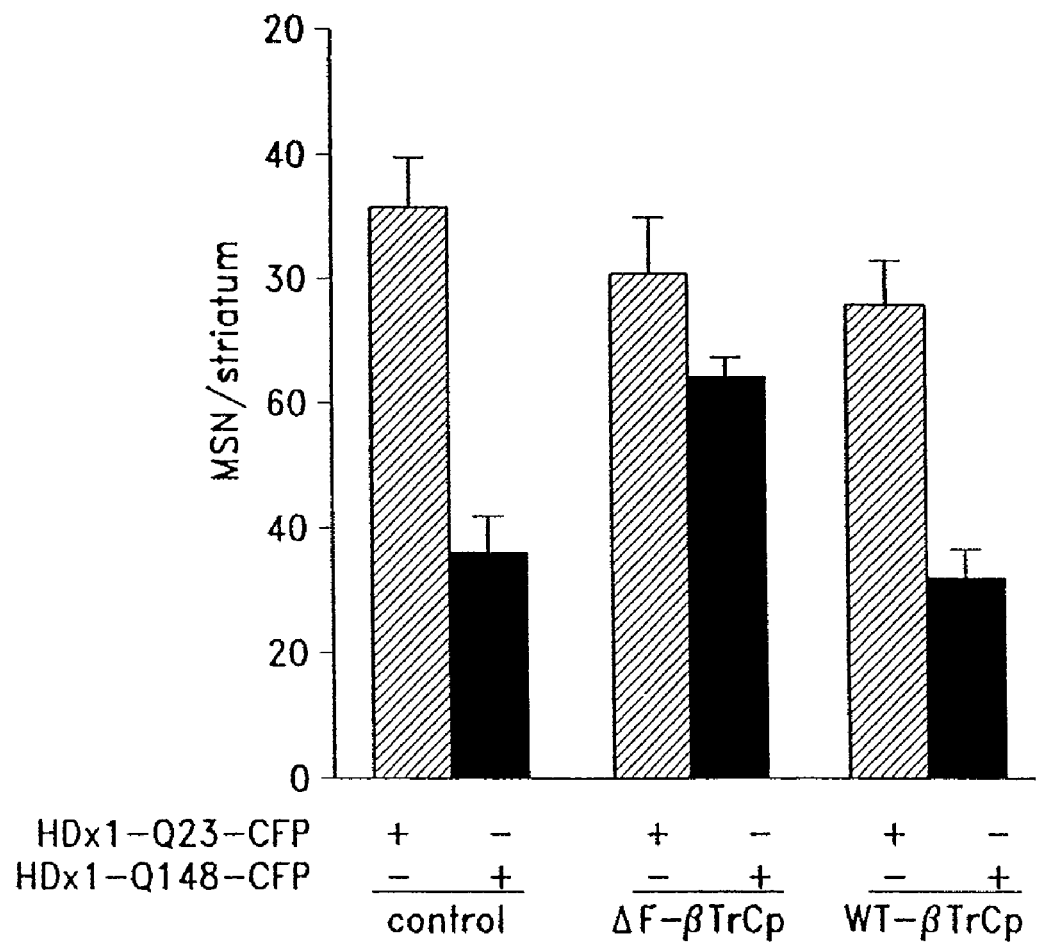

The E3-ubiquitin ligase βTrCP specifically promotes degradation of Iκ-Bα (Spencer et al., 1999). A dominant-negative form of βTrCP (ΔF-βTrCP), which has been shown to block degradation of phosphorylated Iκ-BS, was cotransfected with the NF-κB reporter in PC12 cells. Expression of ΔF-βTrCP abolishes basal and mutant HDx1-induced NF-κB activity (FIG. 7A). As predicted ΔF-βTrCP expression also blocks the toxicity of mutant HDx1 in cultured cells (FIG. 7B, C). Cells expressing ΔF-βTrCP and mutant HDx1 remain intact, whereas cells transfected with mutant HDx1 and control vector become condensed and eventually detach from the cultured dish (FIG. 7B, arrow). Moreover, expression of ΔF-βTrCP in the brain slice assays significantly reduces the toxicity of mutant HDx1 in MSNs (FIG. 7D). WT-βTrCP does not influence the toxicity of mutant HDx1 in MSNs (FIG. 7D). Collectively these data show that blocking IKK activity or degradation of Iκ-B, both of which result in inhibition of NF-κB, can reduce the toxicity of mutant HDx1.

Example 5

Inhibition of IKK by a Small Molecule Inhibitor Reduces Htt Toxicity in Cells

This example illustrates the protection of cells from the toxicity of mutant Htt by an IKK inhibitor.

To examine the effects of a small molecule IKK inhibitor on mutant Htt toxicity, PC12 cells expressing mutant HDx1 are treated with herbimycin or another known IKK inhibitor plus β-gal and NF-κB reporter in six-well plates, essentially as described above in Example 4. Herbimycin is observed to reduce NF-κB expression and blocks the toxicity for mutant HDx1 in the cultured cells.

HEK-293 cells are transfected with mutant HDx1-EGFP, treated with herbimycin treatment or another IKK inhibitor, and analyzed for apoptosis using TUNEL staining as described above in Example 4. The number of TUNEL stained cells is significantly reduced in cells treated with the IKK inhibitor.

P7 rat brain slices are transfected with mutant HDx1 as described above in Example 4 and treated with herbimycin or another known IKK inhibitor. The IKK inhibitor significantly reduces toxicity of mutant HDx1 in MSNs.

Example 6

Identification of Therapeutics for the Treatment of HD

This example illustrates the identification of compounds that can be used to treat or prevent HD.

Compounds to be tested for the potential to be effective therapeutics for HD are provided. As discussed above, the compounds may be, without limitation, small molecules, peptides, polypeptides, or antibodies. In some embodiments the compounds are initially screened for their ability to interact with IKK. Compounds that interact with IKK are then tested for their ability to inhibit IKK activity, for example in an immune complex kinase assay or a gene reporter assay. Compounds that are able to inhibit IKK activity are then tested for their ability to protect cells from the toxic effects of mutant Htt, for example as described above in Example 5.

In other embodiments, compounds are provided that are related to known IKK inhibitors. For example, they may be structurally related. These compounds are first tested for their ability to inhibit IKK activity and, if they appear to be candidate IKK inhibitors, are then tested for their ability to protect cells from the toxic effects of mutant Htt.

In still other embodiments, compounds are tested directly in assays of their ability to protect cells from the toxic effects of mutant Htt, without first directly testing their ability to inhibit IKK.

Compounds that show some efficacy in protecting cells from the toxic effects of mutant Htt may then be tested for their efficacy and toxicity in animal models of HD and in clinical trials on human patients.

Example 7

Treatment of Huntington's Disease

This example illustrates the treatment of a patient suffering from HD.

A patient suffering from or at risk of developing HD is identified and administered an effective amount of a composition comprising an IKK inhibitor. A typical daily dose for an IKK inhibitor of the present invention might range from about 0.01 μg/kg to about 1 mg/kg of patient body weight or more per day, depending on the factors mentioned above, preferably about 10 μg/kg/day to 100 10 μg/kg/day. The appropriate dosage and treatment regimen can be readily determined by the skilled artisan based on a number of factors including the nature of the IKK inhibitor, the route of administration and the patient's disease state. HD treatment efficacy is evaluated by observing delay or slowing of disease progression, amelioration or palliation of the disease state, and remission.

Although the present invention has been described in detail above, it will be understood by the skilled artisan that various modifications can be made without departing from the spirit of the invention. Accordingly, the invention is limited only by the following claims. All cited patents, patent applications and publications referred to in this application are herein incorporated by reference in their entirety.

What is claimed is:

1. A method for protecting cells comprising mutant Htt from the toxicity of mutant Htt, comprising inhibiting I-κB kinase (IKK) activity in said cells by contacting said cells with an IKK inhibitor, wherein said inhibitor inhibits the activation of NF-κB dependent pathways.

2. The method of claim 1, wherein said IKK inhibitor binds to IKKβ.

3. The method of claim 1, wherein said IKK inhibitor blocks interaction of IKKγ with IKKβ and IKKα.

4. The method of claim 1, wherein said IKK inhibitor blocks IKKβ activation.

5. The method of claim 1, wherein said IKK inhibitor is a peptide.

6. The method of claim 1, wherein said IKK inhibitor is a small molecule.

7. The method of claim 6, wherein said small molecule is selected from the group consisting of herbimycin, sodium salicylate, retinoid-related compounds, and cyclopentenone prostaglandins.

8. The method of claim 5, wherein the IKK inhibitor is a NF-κB essential modulator (NEMO) binding peptide.

9. The method of claim 1, wherein the cells are from a patient.

10. The method of claim 9, wherein the patient is a human.

11. The method of claim 1, wherein said cells are neurons.

12. The method of claim 11, wherein said neurons are medium-sized spiny neurons (MSNs).

* * * * *